US006893829B2

(12) United States Patent
Nadler et al.

(10) Patent No.: US 6,893,829 B2
(45) Date of Patent: May 17, 2005

(54) HUMAN LEUKOCYTE 12-LIPOXYGENASE AND ITS ROLE IN THE PATHOGENESIS OF DISEASE STATES

(75) Inventors: Jerry L. Nadler, Charlottesville, VA (US); Rama Natarajan, Hacienda Heights, CA (US)

(73) Assignee: City of Hope, Duarte, CA (US)

( * ) Notice: Subject to any disclaimer, the term of this patent is extended or adjusted under 35 U.S.C. 154(b) by 394 days.

(21) Appl. No.: 09/739,843

(22) Filed: Dec. 20, 2000

(65) Prior Publication Data

US 2001/0009900 A1 Jul. 26, 2001

Related U.S. Application Data

(60) Division of application No. 08/945,744, filed as application No. PCT/US96/06328 on May 3, 1996, now Pat. No. 6,191,169, and a continuation-in-part of application No. 08/434,681, filed on May 4, 1995, now abandoned, which is a continuation-in-part of application No. PCT/US94/00089, filed on Jan. 4, 1994, which is a continuation-in-part of application No. 07/936,660, filed on Aug. 28, 1992, now abandoned.

(51) Int. Cl.$^7$ .......................... C12Q 2/26; G01N 33/50; G01N 33/573; G01N 33/92

(52) U.S. Cl. ............................ 435/7.4; 435/25; 436/63; 436/71

(58) Field of Search ...................... 435/7.4, 25; 436/63, 436/71, 506

(56) References Cited

U.S. PATENT DOCUMENTS

| | | | |
|---|---|---|---|
| 4,849,445 A | | 7/1989 | Schaub |
| 5,128,360 A | * | 7/1992 | Cerami et al. .............. 514/400 |
| 5,238,832 A | * | 8/1993 | Johnson et al. ............. 435/183 |
| 5,246,970 A | * | 9/1993 | Williamson et al. ........ 514/632 |
| 5,250,565 A | * | 10/1993 | Brooks et al. .............. 514/443 |
| 5,686,496 A | | 11/1997 | Anderskewitz et al. |
| 5,731,332 A | | 3/1998 | Anderskewitz et al. |
| 5,795,914 A | | 8/1998 | Konno et al. |
| 5,861,268 A | * | 1/1999 | Tang et al. .................... 435/25 |
| 6,046,224 A | * | 4/2000 | Natarajan et al. ........... 514/381 |

FOREIGN PATENT DOCUMENTS

| WO | 9405777 | 3/1994 |
|---|---|---|
| WO | 9518609 | 7/1994 |

OTHER PUBLICATIONS

HCAPLUS abstract AN 1988:543217 (1988) Natarajan et al.*
HCAPLUS abstract AN: 1995: 245416 (1994) Alanko, J. et al.*
HCAPLUS abstract AN 1989: 451108 (1989) Ibe, B. et al.*
Branch TI BS 23: 45–50, 1998.*
D. W. Foster, In R.G. Petersdorf (ED), Harrison's Principles of Internal Medicine, Morgan Hill, 1983, pp. 661–669.*
G. Wolf et al, Biochem, Biophys. Res. Commun., 176, 902–909, 1991.*
M. Kihara et al, Chem. Abst., 115, 85182 b, 1991.*
M. Itakura et al, Chem. Abst., 115, 1501312, 1991.*
E. N. Ellis et al, Chem. Abst, 115, 150134d, 1991.*
H. P. Hammes et al, Chem Abst. 115, 991462, 1992.*
J. A. Corbett, et al Chem Abst. 115, 249200t, 1992.*
R. Natarajan et al., "Tumor Necrosis Factor and Interleukin–1 are Potent . . . Synthesis", Endocrinology, vol. 125, No. 6, Dec. 1989, 3084–3089.
R. Natarajan et al., "Vascular Smooth Muscle Cells Exhibit . . . Glucose", Biochem. & Biophys. Res. Comm., vol. 187, No. 1, Aug. 31, 1992, 552–560.
R. Natarajan et al., "Mechanism of Angiotensin–II–Induced . . . Cells", Endocrinology, vol. 131, No. 3, Sep. 1992, 1174–1180.
C.P. Bell–Quilley et al., "Renovascular Actions of . . . Lipoxygenases", Journal of Pharm. & Exper. Thera., vol. 267, No. 2, Nov. 1993, 676–682.
J.A. Kim et al., "Evidence that a Leukocyte Type of . . . Cells", Clinical Research, vol. 41, No. 2, (1993), 148A.
E. Sigal et al., "Molecular Cloning and Primary . . . 15–Lipoxygenase", Biochem. & Biophys. Res. Comm., vol. 157, No. 2, Dec. 15, 1988, 457–464.
Rama Natarajan et al., "Elevated Glucose and Angiotersin II . . . Smooth Muscle Cells," Proc. Natl. Acad. Sci., vol. 90, pp. 4947–4951 (Jun. 1993).
Jai–Li Gu et al., "Evidence that a Leukocyte Type of . . . Adrenal Glomerulosa Cells," Endocrinology, vol. 134, No. 1, pp. 70–77 (Jan. 1994).
David Bleich et al., "Interleukin–1β Regulates the Expression of . . . and RIN m5F Cells." Endocrinology, vol. 136, No. 12, pp. 5736–5744 (Dec. 1995).
Balt et al. "2–substituted–1–naphthols as potent 5–lipoxygenase inhibitors with topical antiinflammatory activity" *J. Med. Chem.* 33:360–370 (1990).
Bleich et al. "The stress–activated c–jun protein kinase (JNK) is stimulated by lipoxygenase pathway product 12–HETE in RIN m5F cells" *Biochem. Biophys. Res. Commun,* 230:448–451 (1997).
Cho et al., *J. Med. Chem,* 34:1503–1505 (1991).
Gorins et al. *J. Med. Chem.* 39:4871–4878 (1996).

(Continued)

Primary Examiner—David Saunders
(74) Attorney, Agent, or Firm—Rothwell, Figg, Ernst & Manbeck

(57) ABSTRACT

The present invention relates to a method for inhibiting the etiology of disease in patients having a disease state caused by an excess of 12-lipoxygenase or its products. In particular, the invention provides for administration of a human leukocyte 12-lipoxygenase pathway inhibitor to inhibit disease etiology, to inhibit the proliferation of breast cancer and to increase insulin receptor phosphorylation in a patient having Type II diabetics.

7 Claims, 24 Drawing Sheets

OTHER PUBLICATIONS

Hajjar, D.P. et al., "Signal Transduction in Atherosclerosis: Integration of Cytokines and the Eicossanoid Network" *FASEB J.* 6:2933–2941 (Aug. 1992).
Honn et al., *Cancer Metastasis Rev.* 13:365–396 (1994).
Jost–Vu, E. et al., *Clin. Res. 40*:106 (abstr.) (1992).
Larrue, J., et al., *Biochem. Biophys. Res. Commun. 112*: 242–49 (1983).
Li, Maher, Schubert"A Role for 12–Lipoxygenase in Nerve Cell Death Caused by Glutathione Depletion"*Neuron* 19:453–463 (1997).
Liu et al. "Lipoxygenase metabolites of arachidonic and linoleic acids modulate the adhesion of tumor cells to endothelium via regulation of protein kinase C" *Cell Regulation* 2:1045–1055 (Dec. 1991).
Metz, S. et al., *Proc. Natl. Acad. Sci. USA 82*:198–202 (1985).
Nadler, J.L., et al., "Specific Action of the Lipoxygenase Pathway in Mediating Angiotensin II–induced Aldosterone Synthesis in Isolated Adrenal Glomerulosa Cells" *J. Clin. Invest. 80*:1763–1769 (Dec. 1987).
Natarajan, R., et al., *Hypertension 23* (Supp. I):I142–I147 (1994).
Natarajan, R., et al.,*J. Clin. Endocrinol. Metab. 67*:584–591 (1988).
Natarajan et al., "Arachidonic Acid Metabolites on Renin and Vascular Smooth Muscle Cell Growth" Chapter 26 in: Contemporary Endocrinology: Endocrinology of the Vasculature (Sowers Ed.) Humana Press, Inc., Totowa, NJ, pp. 373–387, (6/96).

Natarajan, Bai, Lanting, Gonzales, Nadler "Effects of High Glucose on Vascular Endothelial Growth Factor Expression in Vascular Smooth Muscle Cells" *Am. J. Physiol.* 273 (*Heart Circ. Physiol.* 42):H2224–H2231 (1997).
Natarajan et al. "Role of 12–lipoxygenase in angiotensin II–induced proliferationin adrenal cells"*Clinical Research* 39(2):184A (1991).
Nishio et al., "Role of the lipoxygenase pathway in phenylephrine–induced vascular smooth muscle cell proliferation and migration" *European J. of Pharmacology* 336:267–273 (1997).
Nozawa et al. *Am. J. Physiol. 259*:H1447–H1780 (1990).
Parthasarathy, S. et al., *Proc. Natl. Acad. Sci. USA 86*:1046–1050 (1989).
Rao, G.N., et al., *Oncogene* (1993) 8:2759–2764.
Stern, N., et al., "Selective inhibition of angiotensin II–mediated vasoconstriction by lipoxygenase blockade"*Am. J. Physiol. 257*:H434–H443 (1989) (Abstr.).
Wen et al., "Evidence that angiotensin II and lipoxygenase products activate c–jun $NH_2$–terminal kinase" *Circ. Res.* 81:651–655. (1997).
Wen et al., *Am. J. Physiol,* 271 (Cell Physiol. 40): C1212–C1220 (1996).
Yu, C.L., "Serum Stimulation of NIH 3T3 Cells Induces the Production of Lipids Able to Inhibit GTPase–Activating Protein Activity" *Mol. Cell Biol. 10*:6683–6689 (1990).
Johnson et al., "Antioxidant With marked Lipid– and Glucose–Lowering Activity in Diabetic Rats and Mice", Diabetes, vol. 42, Aug. 1993 1179–1186.

* cited by examiner

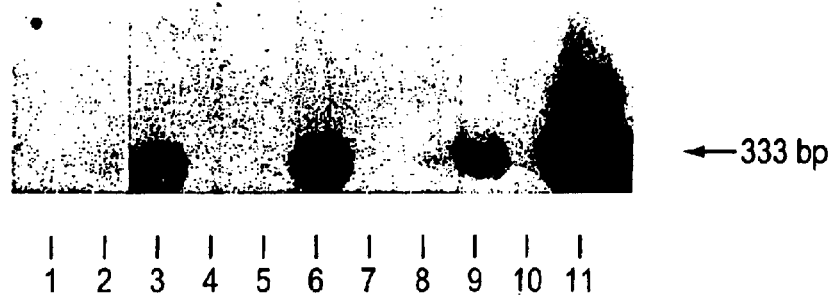
FIG. 1A
FIG. 1B
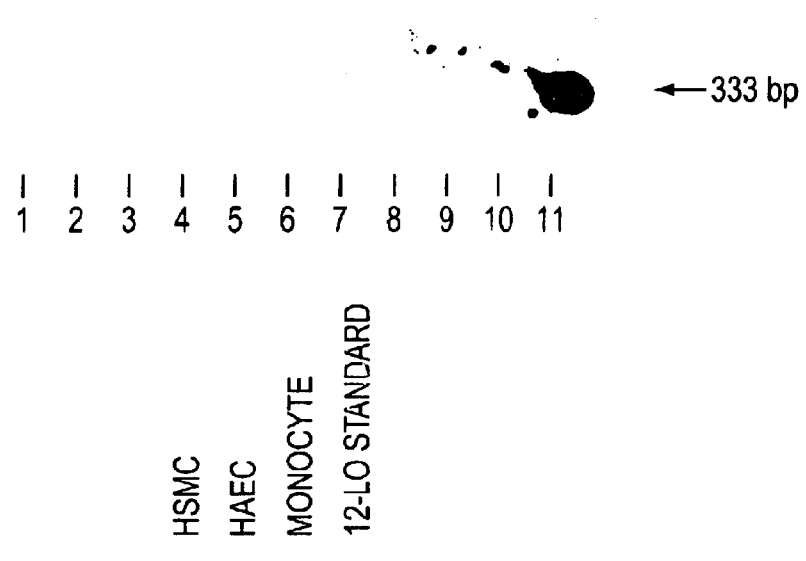
FIG. 2

— 42 kD

— 42 kD

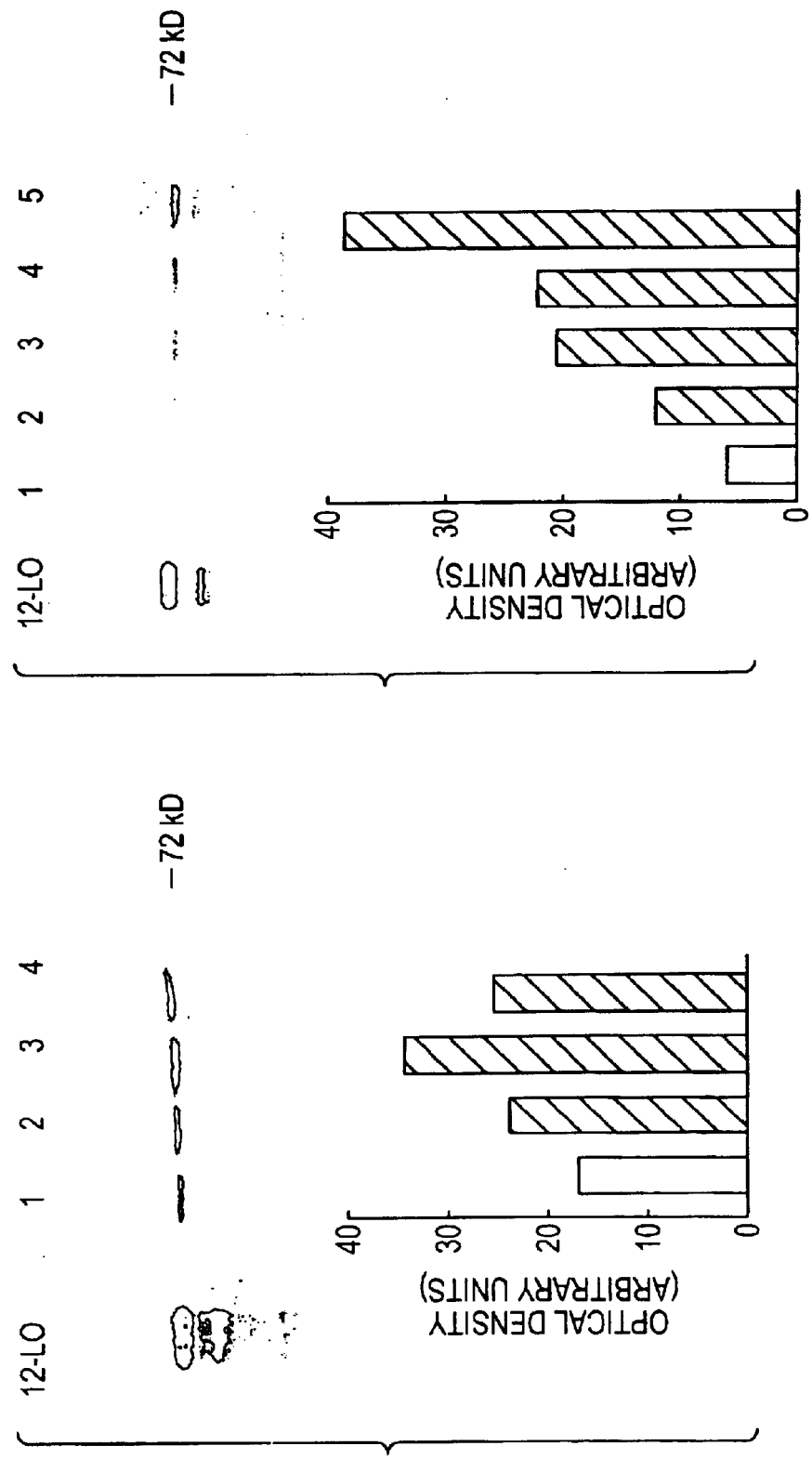

1 2 3 4 5 6 7 8

↑ 5.5mM GLUCOSE   ↑ 2.5mM GLUCOSE   ↑ 2.5mM GLUCOSE PLUS BAICALEIN $10^{-6}$M

←—75 kD

HUMAN LEUKOCYTE 12-LIPOXYGENASE AND ITS ROLE IN THE PATHOGENESIS OF DISEASE STATES

RELATED APPLICATIONS

This application is a divisional of U.S. Ser. No. 08/945,744, filed Nov. 3, 1997, now U.S. Pat No. 6,191,169 which is a 371 of PCT/US96/06328, filed May 3, 1996, and a continuation-in-part of U. S. application Ser. No. 08/434,681, filed May 4, 1995 now abandoned, which is a continuation-in-part of PCT/US94/00089, filed Jan. 4, 1994, which is a continuation-in-part of U.S. application Ser. No. 07/936,660, filed Aug. 28, 1992, now abandoned.

GOVERNMENT RIGHTS STATEMENT

This invention was made with government support under Grant No. DK 39721 RO1 awarded by the National Institutes of Health. The government has certain rights in the invention.

TECHNICAL FIELD

This invention pertains to a human leucocyte type of 12-LO and its role in the pathogenesis of several major disease states.

ABBREVIATIONS

| | |
|---|---|
| AA = | Arachidonic acid |
| AII = | Angiotensin II |
| EGF = | Epidermal Growth Factor |
| EN = | Fibronectin |
| GAPDH = | Glyceraldehyde-3-phosphate dehydrogenase |
| GF = | Growth Factor |
| HAEC = | Human Aortic Endothelial Cells |
| HETE = | Hydroxyeicosatetraenoic Acid |
| 12 HETE = | 12-Hydroxyeicosatetraenoic Acid |
| HG = | High Glucose |
| hl 12-LO = | Human Leukocyte 12-Lipoxygenase |
| hl 15-LO = | Human Leukocyte 15-Lipoxygenase |
| HODE = | Hydroxyoctadecadiefloic acid |
| 12-HPETE = | 12-Hydroperoxyeicosatetraenoic Acid |
| HSMC = | Human Aortic Smooth Muscle Cells |
| HPLC = | High Pressure Liquid Chromatography |
| IL-1 = | Interleukin-1 |
| LDL = | Low Density-Lipoprotein |
| LO = | Lipoxygenase |
| 12-LO = | 12-Lipoxygenase |
| 15-LO = | 15-Lipoxygenase |
| MAPK = | Mitogen Activated Kinase |
| mmLDL = | Minimally Modified Low Density Lipoprotein |
| MO = | Monocytes |
| NIDDM = | Non-insulin Dependent Diabetes Mellitus |
| NG = | Normal Glucose |
| PDGF = | Platelet Derived Growth Factor |
| PKC = | Protein Kinase C |
| p1 12-LO = | Human platelet 12-Lipoxygenase |
| PVSMC = | Porcine Vascular Smooth Muscle Cells |
| RT-PCR = | Reverse Transcriptase Polymerase Chain Reaction |
| SMC = | Smooth Muscle Cells |
| TGFB = | Transforming Growth Factor Beta |
| TNF = | Tumor Necrosis Factor 1 |
| VSMC = | Vascular Smooth Muscle Cells |

BACKGROUND OF THE INVENTION

The three mammalian lipoxygenases are named according to the carbon position (1, 2 or 3) at which they oxygenate arachidonic acid (4). There is increasing evidence that certain LO enzymes are involved in the pathogenesis and acceleration of atherosclerosis by inducing oxidation of LDL to its atherogenic form (5,6) and increasing the growth or migration of smooth muscle cells (1, 7–9). In addition, evidence suggests that a 12-LO protein plays a role in mediating angiotensin II (AII) induced vascular and adrenal actions (10–12). Recent studies indicate that at least two forms of 12-LO exist, i.e., pl 12-LO cloned from human erythroleukemia cells (2,13) and a porcine leukocyte 12-LO which has been isolated and cloned from porcine mononuclear cells, pituitary (14) and bovine tracheal cells (15).

Applicants have demonstrated the presence of a leukocyte type of 12-LO in human adrenal glomerulose cells (3). The human 15-LO has been purified from human and rabbit reticulocytes (16,17). The human platelet and porcine leukocyte type 12-LO share 65% amino acid homology (13). However, porcine leukocyte type 12-LO is highly homologous to human 15-LO (86%) (14). Recently, it has been shown that 15-LO is expressed in macrophages of human atherosclerotic lesions but not in unstimulated monocytes (18).

SUMMARY OF THE INVENTION

This application describes evidence for the presence of a human leucocyte type of 12-LO enzyme (hl 12-LO) and its role in the pathogenesis of several major disease states or processes, including atherosclerosis, breast cancer, autoimmune and inflammatory disease, diabetic vascular and kidney disease and insulin resistance. There are several features of this unique enzyme that can link several seemingly diverse conditions.

1. hl 12-LO can utilize arachidonic and linoleic acid as fatty acid substrates generating hydroperoxides and other lipid mediators which can activate important signal transduction pathways commonly associated with these disorders. These mediators include (a) kinases such as specific isoforms of protein kinase C and mitogen activated kineses (MAPK), (b) transcription factors such as NFkB and oncogenes which have clearly been implicated in inflammatory and autoimmune conditions, atherosclerosis, cancer growth and metastasis.

2. Activation of the hl 12-LO enzyme can itself generate superoxide anions which can lead to the propagation of free radical processes which could accelerate the oxidative modification of lipids and proteins. These processes are involved in the pathogenesis of inflammatory, neoplastic and atherogenic conditions.

3. The hl 12-LO enzyme is strategically located. Evidence is presented showing the presence of the leucocyte type 12-LO in human monocytes, aortic vascular smooth muscle and endothelial cells, cardiac myocytes, skeletal muscle, the kidney and breast cancer cells and beta cells of pancreatic islets. These sites of activity of this enzyme allow a tissue specific role in leading to pathologic states. For instance, in the beta cells of the pancreatic islets, activation of 12-LO activity by inflammatory cytokines (e.g., IL-1) could explain the selective dysfunction and destruction of the beta or insulin producing cells of the pancreas. Furthermore, activation or increased expression of the 12-LO pathway by glucose in the beta cells could explain the dysfunctional secretion of insulin in the common form of adult diabetes (non-insulin dependent diabetes).

4. Factors increasing 12-LO expression and activity are linked to inflammatory, atherosclerotic, renal and neoplastic disease.

The factors demonstrated to increase the activity and expression of 12-LO include, (a) inflammatory cytokines associated with autoimmune disease (Type I diabetes) atherosclerosis and neoplastic growth such as interleakin-1β (IL-1), (b) growth factors such as platelet derived growth factor (PDGF) and angiotensin II (AII) which have been implicated in accelerated vascular and kidney disease, and (c) hyperglycemia which has been linked to the microvascular (eye, kidney and nerve) and microvascular (heart attack, stroke and peripheral vascular disease) complications of both type I or type II diabetes.

5. Applicants have found that glucose which accounts for much of the acquired insulin resistance in diabetes increases 12-LO activity and expression in all tissues tested. Therefore, 12-LO activation could provide a common link between glucose-induced oxidative stress and development of end-organ dysfunction or damage.

Pursuant to this invention, blockade of the hl 12-LO expression or enzyme activation provides novel treatments to prevent these disease states.

Identification of 12-LO in Normal HSMC, HAEC and MO

Applicants have now evaluated the precise type of LO present in unstimulated human aortic smooth muscle cells (HSMC), endothelial cells (HAEC) and monocytes (MO). Furthermore, since AII can increase the expression of 12-LO in human adrenal cells, applicants have also evaluated the effects of AII on 12-LO regulation in HSMC. Finally, applicants determined whether immunohistochemical analysis of atherosclerotic lesions demonstrates the presence of a leukocyte type of 12-LO. The results show that a 12-LO similar to that found in human adrenal glomerulose is expressed in the normal HSMC, HAEC and MO. Furthermore, this 12-LO is markedly upregulated by AII in HSMC and is present in human atherosclerotic lesions.

DESCRIPTION OF FIGS. 1 TO 7

FIGS. 1A and 1B illustrate RT-PCR analysis of leukocyte 12-LO RNA in HAEC, HSMC, and MO. FIG. 1A illustrates RNA samples that were amplified for 40 cycles with leukocyte specific 12-LO primers Membranes were hybridized with porcine leukocyte 12-LO oligonucleotide probe. Lane 1 is a marker, Lanes 2, 5, 8 are negative controls without template, lane 3 represents total RNA from HAEC, with porcine leukocyte 12-LO primer, lane 4 with GAPDH primers. Lane 6 represents total RNA from HSMC with porcine leukocyte 12-LO primers, lane 7 with GAPDH primers. Lane 9 represents total RNA from MO with porcine leukocyte 12-LO primers. Lane 10 with GAPDH primers, and lane 11 is a positive control using the porcine leukocyte 12-LO cDNA.

FIG. 1B illustrates the same RNA samples which were amplified for 40 cycles with human specific 15-LO primers. Membranes were hybridized with human 15-LO oligonucleotide. Only the 333 base pair product from amplification of the 15-LO cDNA (positive control) is shown.

FIG. 2 illustrates the expression of leukocyte 12-LO protein (72 kD) in normal HAEC, HSMC, and MO. Cytosol fractions from HAEC, HSMC, and MO were electrophoresed along with authentic porcine 12-LO protein and subjected to Western immunoblotting.

FIG. 3A illustrates the effect of AII on 12-HETE release by HSMC. HSMC were grown to confluency. Serum was removed and cells were incubated in media 199 containing 0.4% fetal bovine serum (FBS) and 0.2% BSA for 18 hours. Cells were then washed with DME media and incubated for 20 minutes in DME media containing 0.2% BSA. AII was added to the cells for five and ten minutes at the concentrations of $10^{-9}$ and $10^{-8}$ mol/L. Media were collected for HETE assay.

*$p<0.05$ vs control n=4

FIG. 3B illustrates the effect of AII on cell-associated 12-HETE levels in HSMC. After collecting supernatants, cells were washed with ice-cold PBS and harvested by scraping for the assay of cell-associated HETEs.

*$p<0.02$ vs control n=4

FIGS. 4A and 4B illustrate the regulation of leukocyte 12-LO protein expression by AII in HSMC. FIG. 4A is an immunoblot showing regulation by AII. FIG. 4B is a bar graph representation of densitometric analysis of immunoblot in FIG. 4A. Cells were grown in medium 199 containing 20% FBS and serum-depleted for 24 hours by placing in medium 199 containing 0.4% FBS and 0.2% BSA. Cells were treated with AII at the concentration of $2 \times 10^{-7}$ mol/L for 24 to 48 hours. Cells were washed with PBS and harvested by scraping. Cell pellets were lysed and cytosol fractions were electrophoresed.

FIGS. 5A and 5B illustrate the regulation of leukocyte 12-LO mRNA levels by AII in HSMC using RT-PCR. FIG. 5A is the autoradiogram of the blot hybridized with 12-LO oligonucleotide probe. FIG. 5B is etidium bromide stained agarose gel. Total RNA was extracted from culture HSMC incubated in low serum conditions with AII ($2 \times 10^{-7}$ mol/L) for different time-period shown. RNA samples were amplified for 40 cycles with leukocyte 12-LO primers or GAPDH primers.

FIGS. 6A and 6B illustrate microphotographs of a histologic section of an artery obtained from a below-the-knee amputation specimen from a patient with extensive arteriosclerosis. Avidin-biotin complex immunohistochemical technique was used to detect 12-LO with purified specific rabbit anti-sera. Intense staining of endothelial cells (arrowhead), cells present in endothelial thickening (small arrow) and, to a lesser degree, on the smooth muscle cells (larger arrow) were noticed in FIG. 6A. Pre-immune rabbit sera was used at the same concentration s negative control (FIG. 6B). (×200 magnification).

FIGS. 7A and 7B illustrate immunostaining of human coronary lesions using antibody to 12-lipoxygenase. Shown is a cross-section of a human left coronary artery with an advanced atherosclerotic plaque (note the cholesterol crystals in the core region) reacted with either 12-LO antibody (FIG. 7A) or pre-immune antisera (FIG. 7B). The darkest immunoreactivity is seen in adventitial blood vessels associated with pericytes. The medial smooth muscles cells are also immunoreactive. Lighter immunoreactivity is seen in intimal cells in plaque and non-plaque areas.

Figure 11:
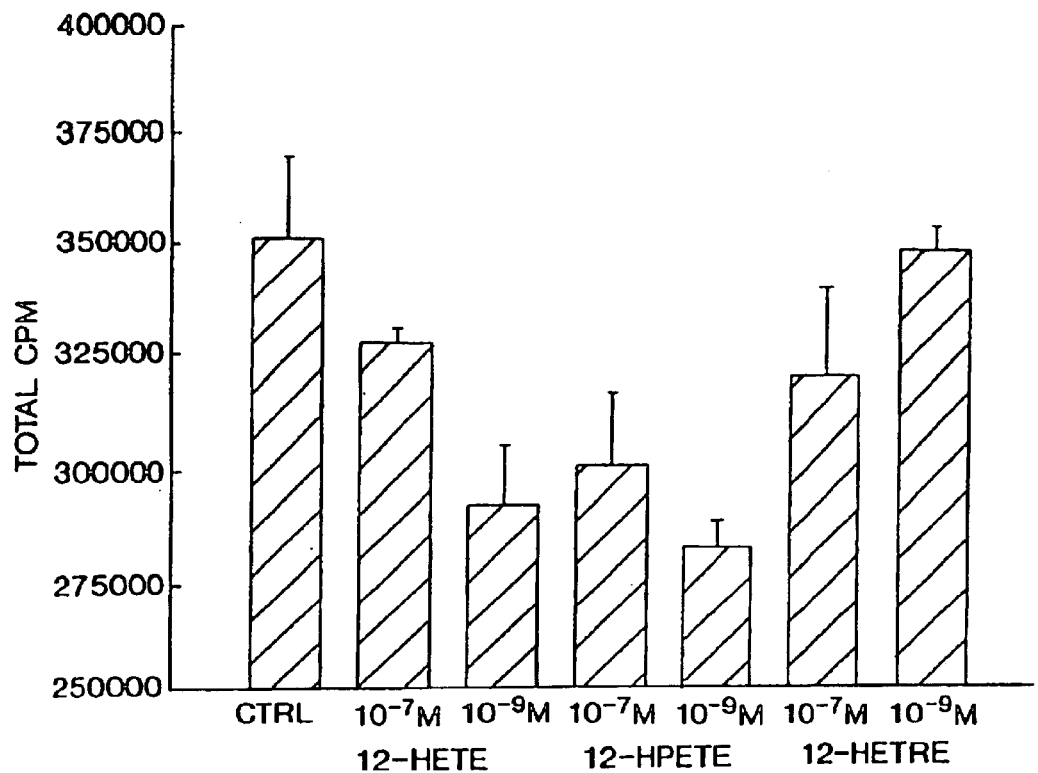

FIG. 11 provides data on the effects of 12-LO products on DNA synthesis in RINm5F cells.

Figure 12:
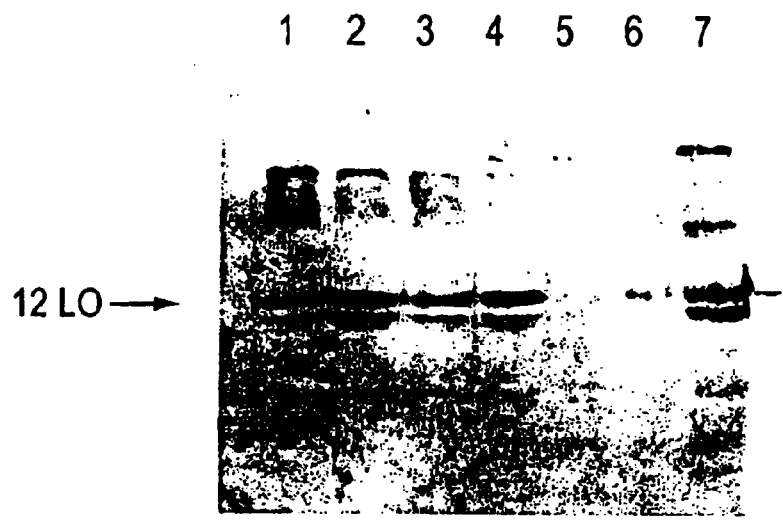

FIG. 12 is a Western blot of proteins isolated from RINm5F cells showing the effect of IL-1β on 12-LO protein expression.

Figure 13:
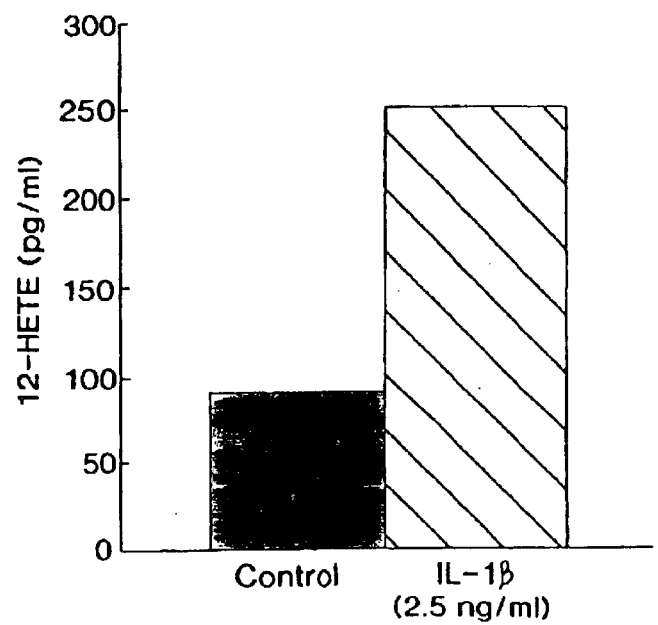

FIG. 13 illustrates the effects of IL-1β on 12-HETE production in rat islets.

Figure 14A:
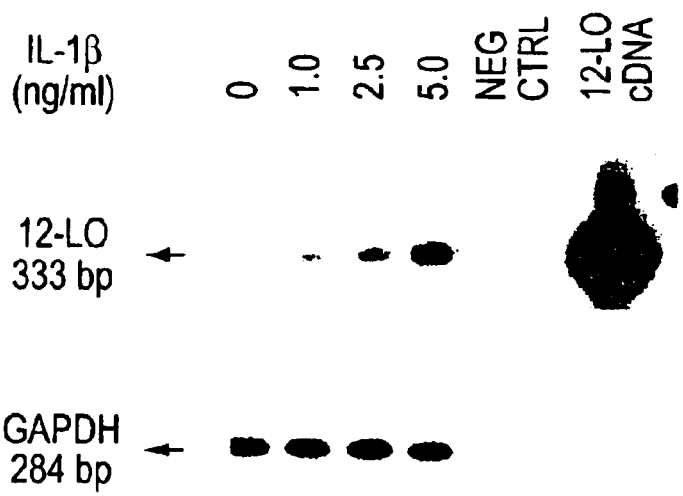
Figure 14B:
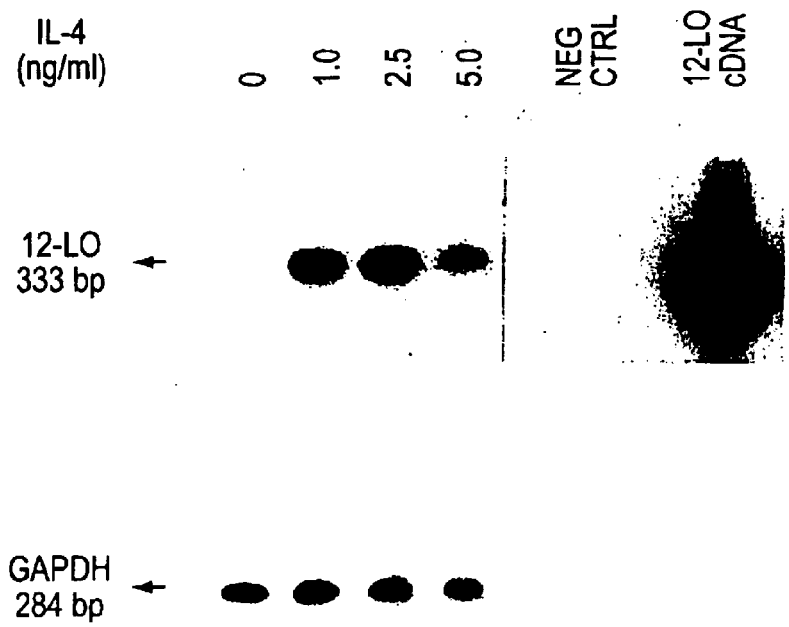
Figure 14C:
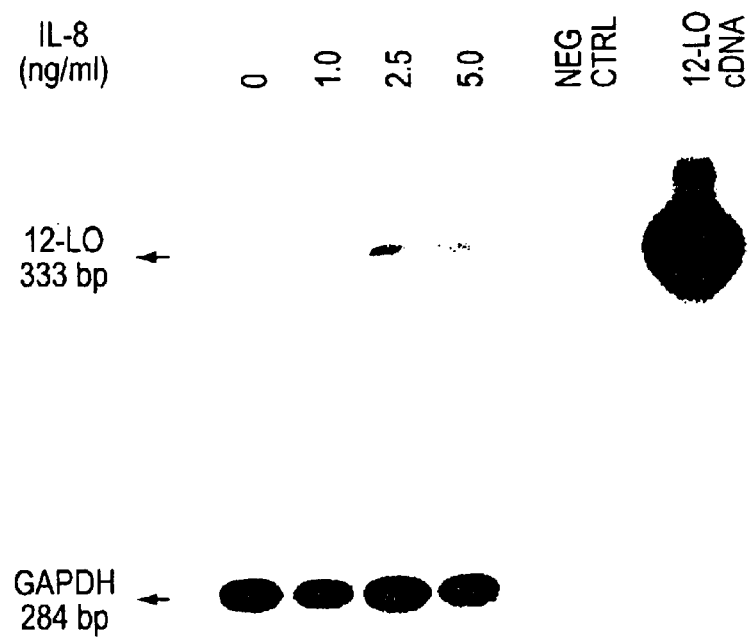

FIG. 14A shows the effects of IL-1B on 12-LO mRNA expression in porcine aortic smooth muscle cells. FIGS. 14B and 14C show the same information for IL-4 and IL-8, respectively.

Figure 15:
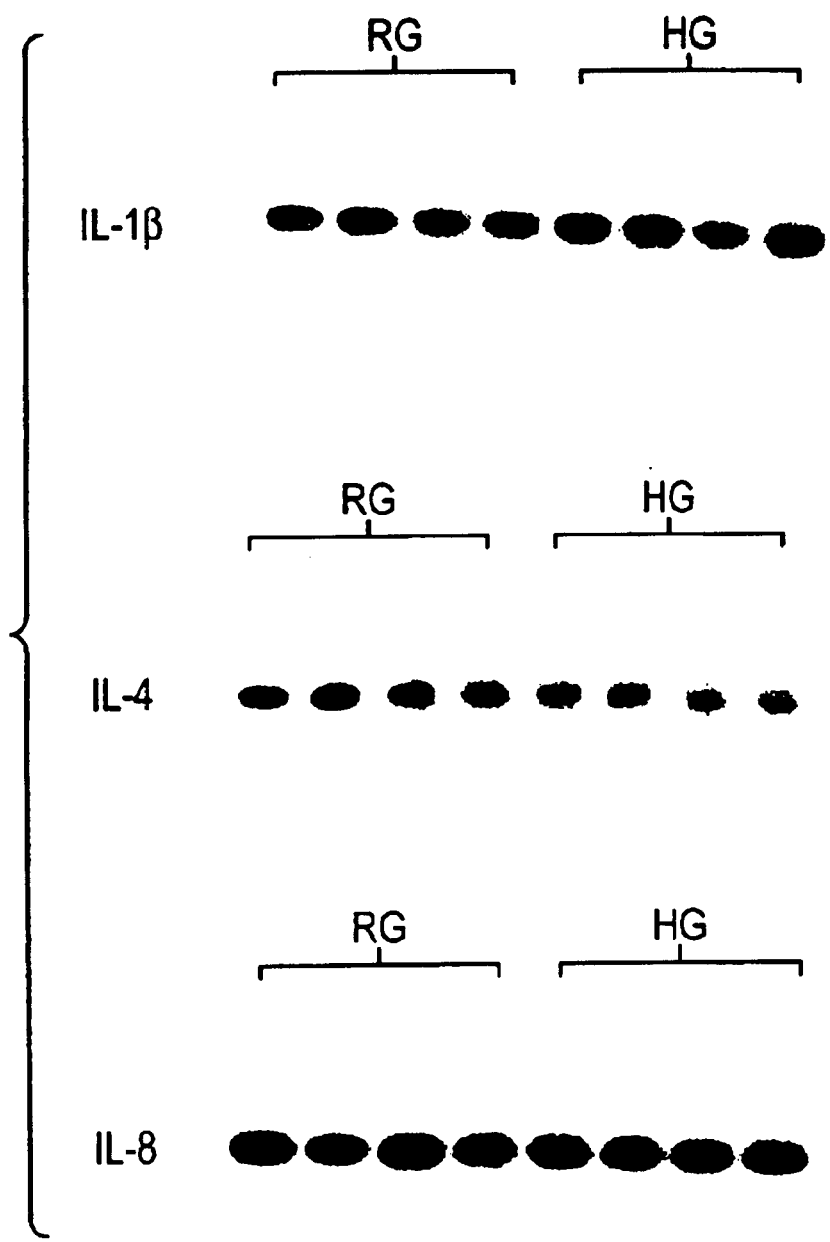

FIG. 15 illustrates data on mRNA for the marker GAPDH.

FIG. 16 illustrates the effect of IL-4 on leukocyte 12-LO protein expression in porcine vascular smooth muscle cells.

FIG. 17 shows the same data as FIG. 16 for IL-8.

Figure 18:
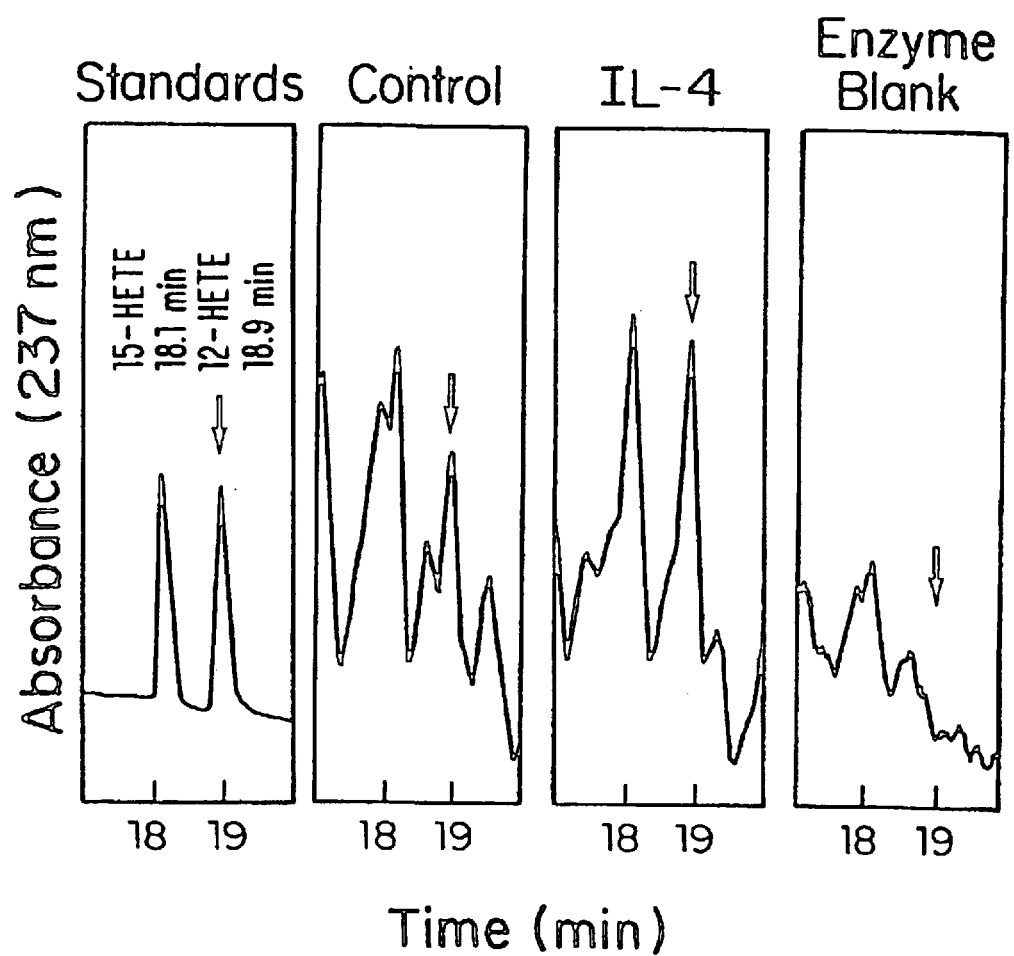

FIG. 18 provides data on the effect of IL-4 on 12-LO activity in porcine smooth muscle cells.

Figure 19:
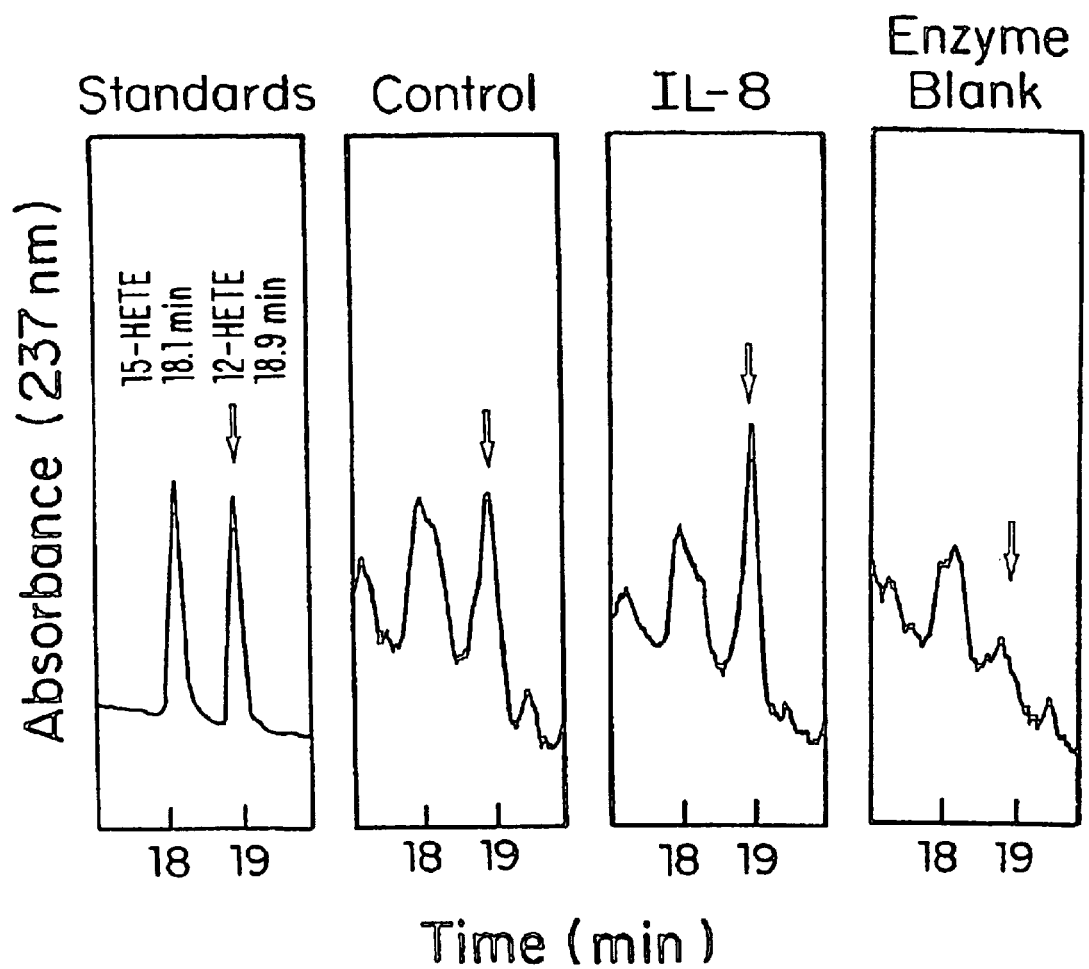

FIG. 19 shows the same data as FIG. 18 for IL-8.

Figure 20:
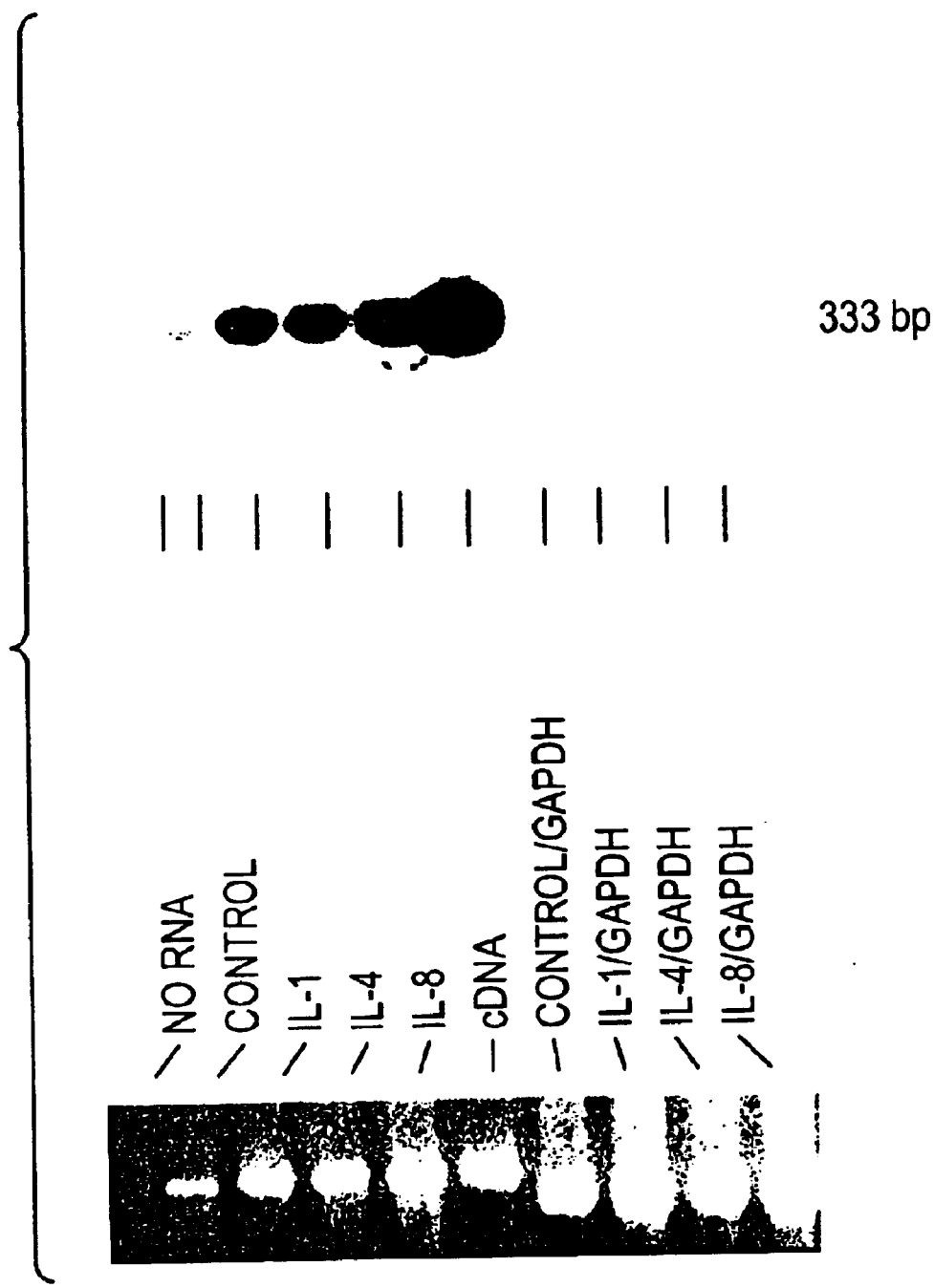

FIG. 20 illustrates data regarding the upregulation of human leukocyte 12-LO by IL-1, IL-4 and IL-8.

Figure 21:
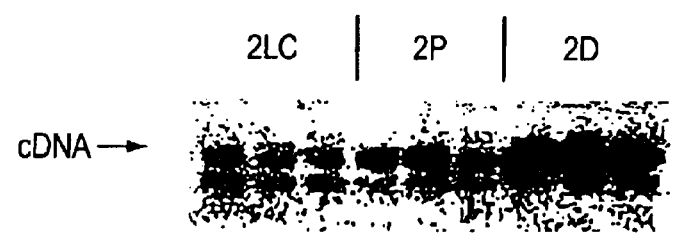

FIG. 21 shows increases in 12-LO mRNA in the pancreatic islets of increasingly diabetic rats.

Figure 22:
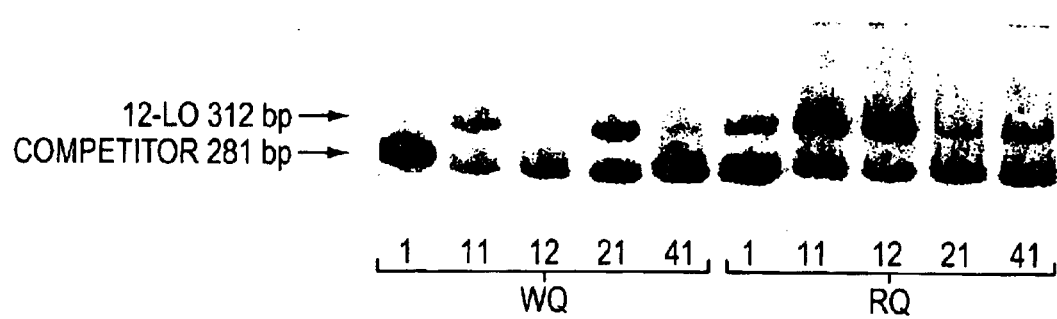

FIG. 22 shows levels of 12-LO mRNA in diabetic and non-diabetic ZDF rats.

Figure 23:
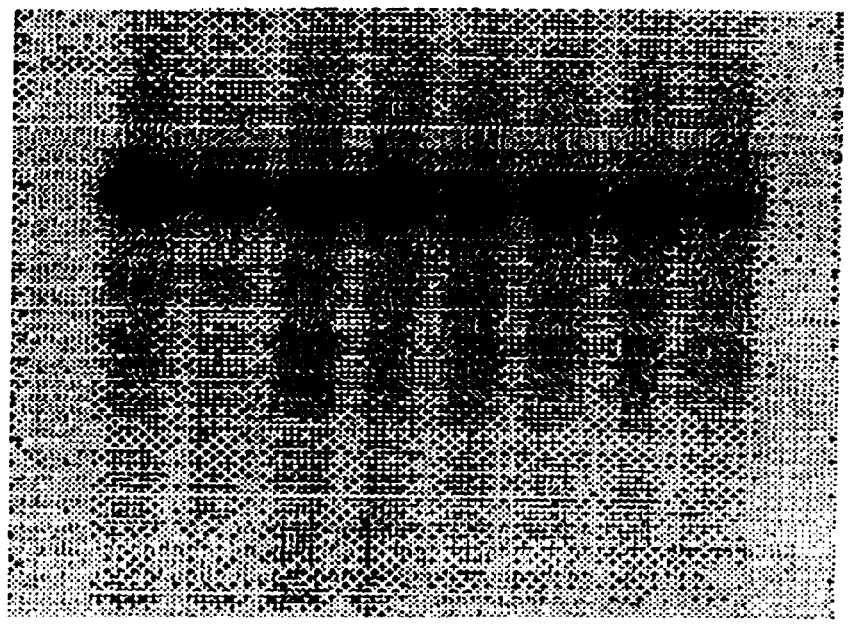

FIG. 23 present data pertaining to rat fibroblasts overexpressing the human insulin receptor at different glucose concentrations in the presence or absence of baicalein.

Figure 24:
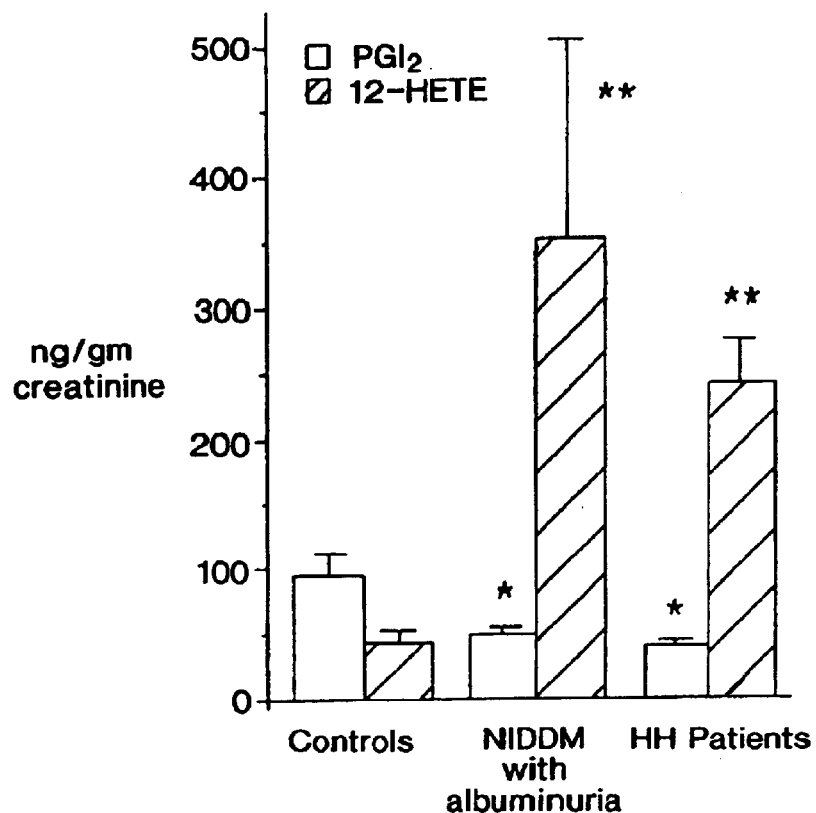

FIG. 24 shows data regarding the HETE/PGI$_2$ ratio in different diabetic groups.

Figure 25:
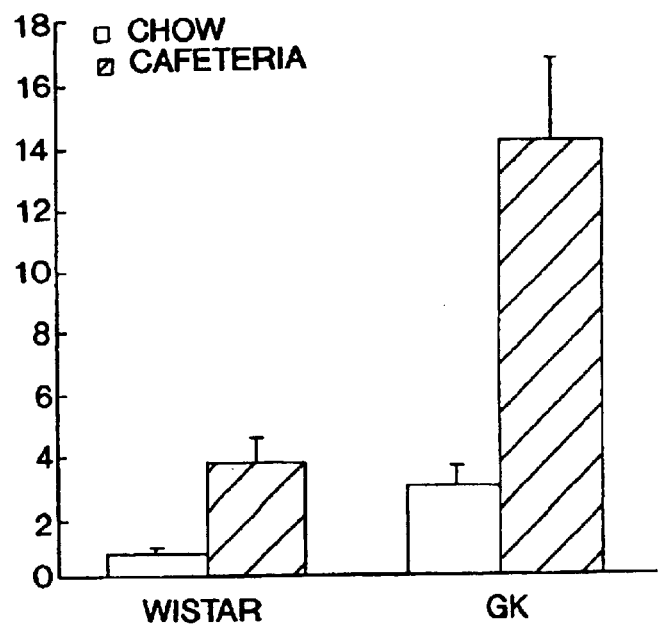

FIG. 25 provides data regarding Wistar and GK rats under Chow and Cafeteng diet conditions.

Figure 26:
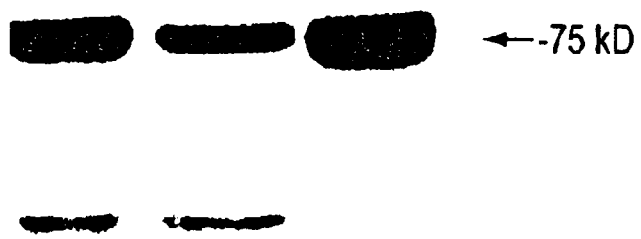

FIG. 26 shows increased amounts of 12-LO in diabetic (GK) rats compared to normal (Wistar rats).

Figure 27:
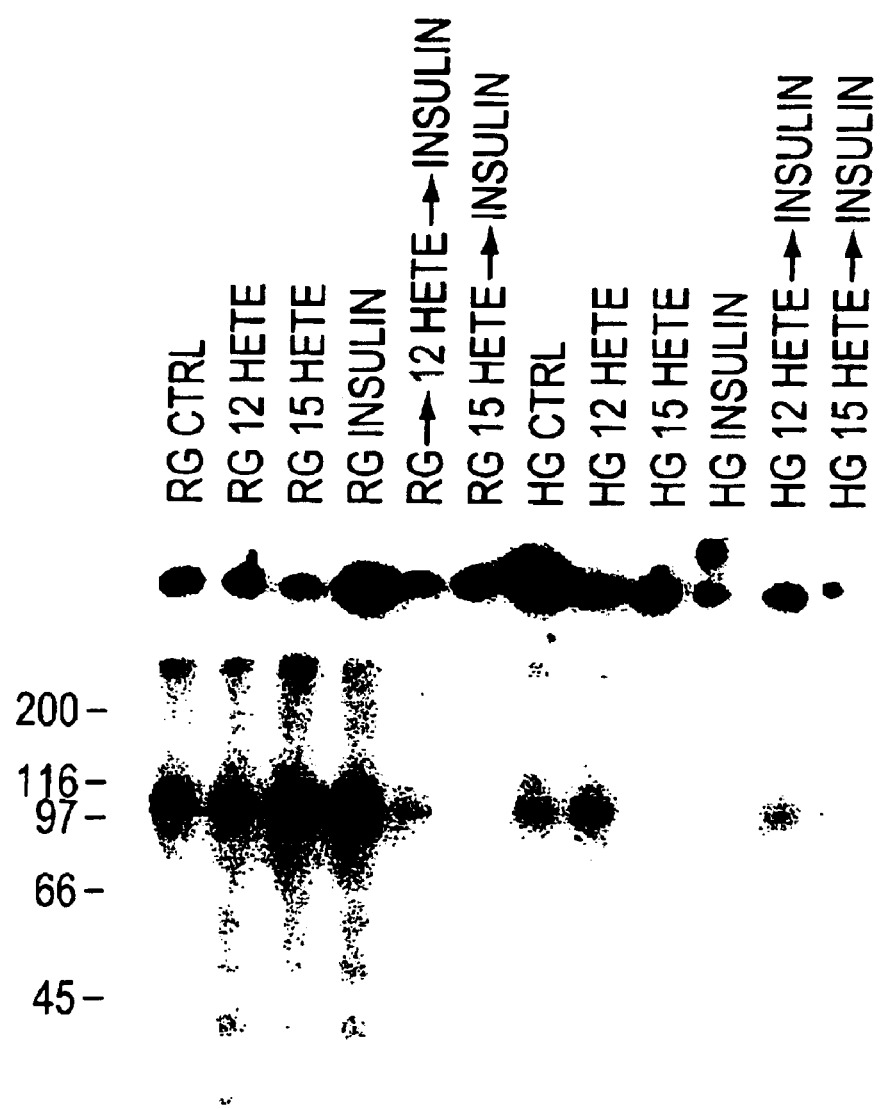

FIG. 27 shows data demonstrating increase in phosphorylation of the insulin receptor β subunit by insulin as affected by 12-HETE.

Figure 28A:
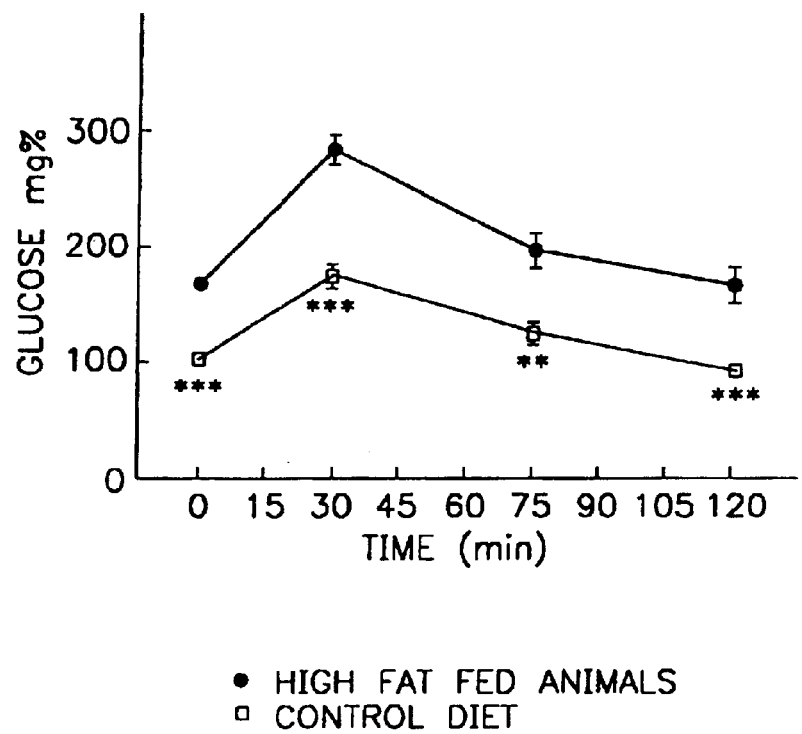
Figure 28B:
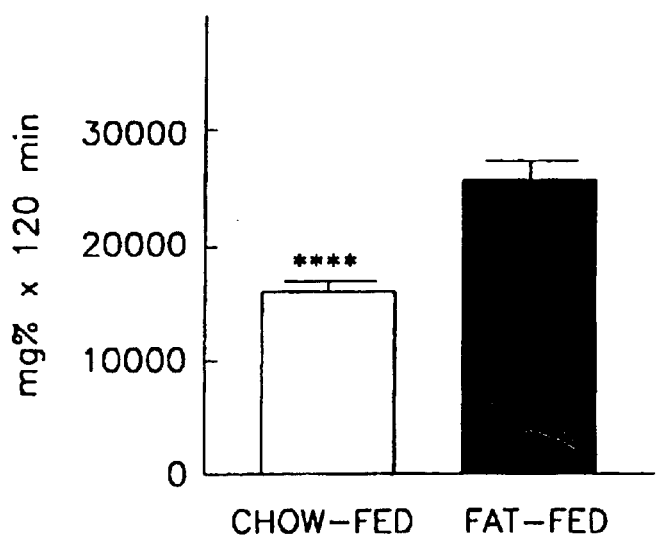

FIG. 28A shows glucose levels in rats fed a high fat diet versus a control diet. FIG. 28B represents the area under the glucose-tolerance curve in FIG. 28A for high fat fed rats and control rats.

Figure 29:
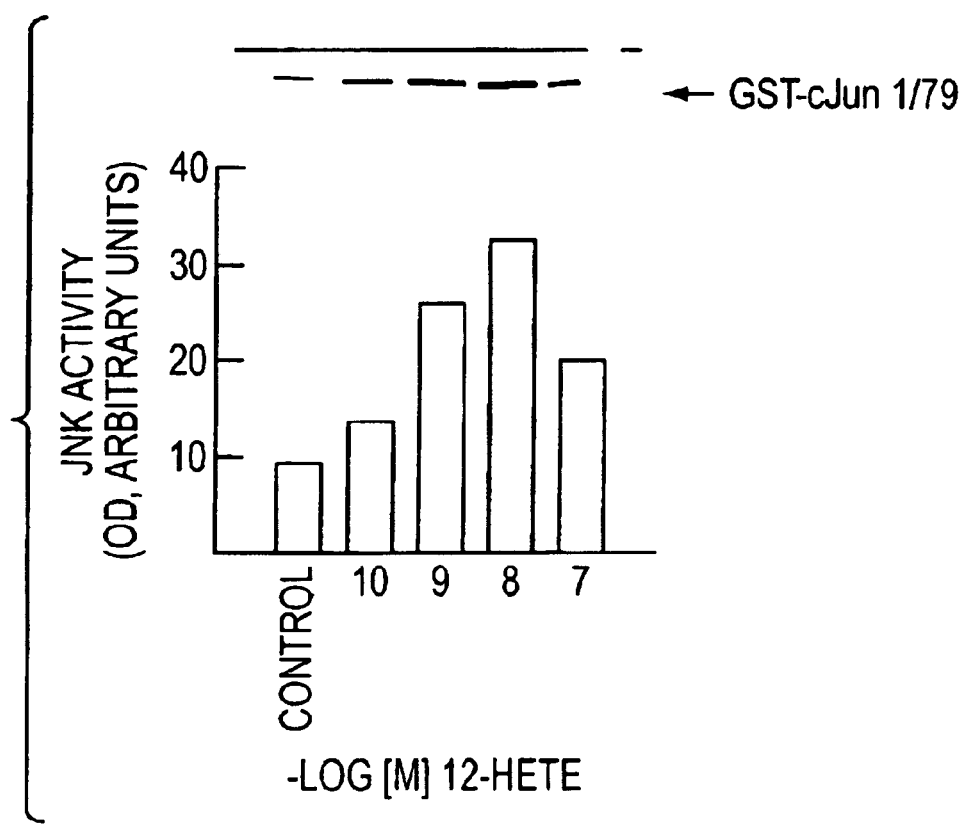

FIG. 29 illustrates JNK activity as a function of 12-HETE concentration.

Figure 30:
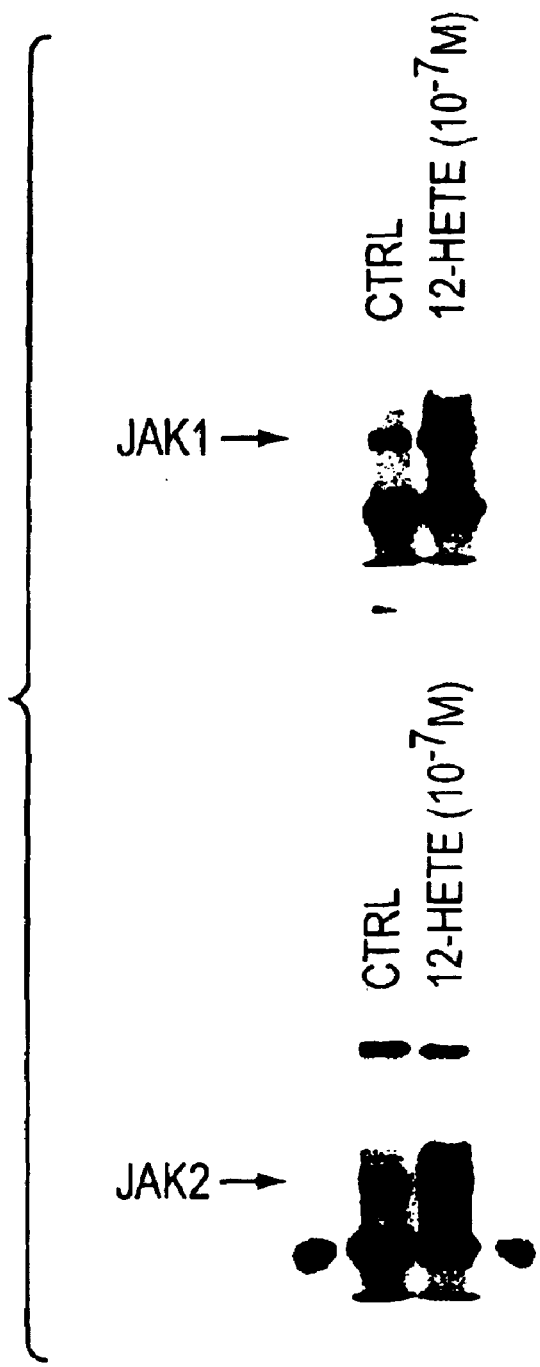

FIG. 30 is an immunoblot showing JAK1 and JAK2 bands under control and $10^{-7}$M 12-HETE conditions.

Experimental Procedure

The lipoxygenase (LO) pathway has been implicated in leading to accelerated atherosclerosis. The precise form of 12-LO expressed in adrenal glomerulose pancreatic islets is described in application PCT/US94/00089. This application establishes that a similar precise type of hl 12-LO is present in unstimulated human aortic smooth muscle cells (HSMC), endothelial cells (HAEC) and monocytes (MO). In this study, the specific reverse-transcriptase polymerase chain reaction (RT-PCR) method was used to analyze the type of LO mRNA expressed in normal HSMC HAEC and MO. In all three cell types, a 333 base pair band was seen using primers and probes specific for the leukocyte type of 12-LO suggesting that a leukocyte type of 12-LO is expressed in these cell types. Western immunoblotting analysis in cultured HSMC, HAEC and MO using a polyclonal peptide antibody to leukocyte type of 12-LO showed a specific 72 kD band which is identical to the molecular weight of the leukocyte type of 12-LO. Angiotensin II (AII) added to normal HSMC increased 12-LO activity and expression. Immunohistochemical analysis of atherosclerotic lesions also indicated the presence of a leukocyte type of 12-LO. These results indicate that a leukocyte type of 12-LO RNA is expressed in HSMC, HAEC and MO. Also, AII upregulates 12-LO activity and expression in HSMC supporting a role for this 12-LO pathway in human vascular disease.

1. Cells and Cultures

HAEC and HSMC were isolated from aortic specimens obtained from the heart donors in UCLA heart transplant program. HAEC at passages 5–9 and HSMC at passages 3–7 were used. HAEC were grown in medium 199 containing 20% FBS supplemented with EC growth supplement (20 mg/ml) and heparin (90 µg/ml). HAEC were identified by their typical cobblestone morphology, presence of Factor VIII-related antigen and uptake of acetylated LDL labeled with 1,1'-dioctadecyl-1-3,3,3',3'-tetramethylindocarbocyanine perchlorate (Dil-acetyl-LDL) (19). HSMC were grown in medium 199 containing 20% FBS and identified morphologically and immunohistochemically using HHF35, which was then visualized by a fluorescently labeled second antibody or using a biotin-streptavidin complex immunoperoxidase system (20). Monocytes were obtained from a large pool of healthy donors by a modification of the Recalde method (21).

HSMC and HAEC monolayers were washed twice with ice-cold PBS and then processed for RNA extraction or western analysis as described below. For hydroxyeicosatetraenoic acid (HETE) assay, approximately 24 hours prior to an experiment, the medium was replaced with medium 199 containing 0.4% FBS and 0.2% BSA.

2. cDNAs

Recombinant Bluescript plasmid containing the cDNA for human reticulocyte 15-LO was kindly provided by Dr. E. Sigal (Syntex Co., Palo Alto, Calif.). pUC19 plasmid containing the cDNA for porcine leukocyte 12-LO was obtained as described previously (14). Bluescript plasmid containing the cDNA for human platelet 12-LO was kindly provided by Prof. Bengt Samuelson (Karolinska Institute, Stockholm, Sweden) (2).

3. Oligonucleotide primers and probes for PCR.

β$_2$-Macroglobulin oligonucleotides were a kind gift of Dr. Perrin White (Cornell University Medical College, New York, N.Y.). Other oligonucleotides including human glyceraldehyde-3-phosphate dehydrogenase (GAPDH) oligonucleotides were synthesized on an Applied Biosystems (Foster City, Calif.) DNA synthesizer and were purified by polyacrylamide gel electrophoresis. The sequences of oligonucleotides are listed in Table 1 and were designed based on known gene sequences (2, 14, 22, 23) and selected from regions displaying most divergence between porcine 12-LO and 15-LO sequences (13).

TABLE 1

| | Primers and probes for amplification and detection | | |
|---|---|---|---|
| | | Sequence (5'-3') | Position |
| Human 15-LO | 5' primer | AACTCAAGGTGGAACTACCGGAG (SEQ ID NO. 1) | 146–168 |
| | 3' Primer | ATATAGTTTGGCCCCAGCCATATTC (SEQ ID NO. 2) | 453–477 |
| | Probe | AGGCTCAGGACGCCGTTGCC (SEQ ID NO. 3) | 306–326 |

TABLE 1-continued

Primers and probes for amplification and detection

|  |  | Sequence (5'-3') | Position |
|---|---|---|---|
| Porcine Leukocyte 12-LO | 5' Primer | TTCAGTGTAGACGTGTCGGAG (SEQ ID NO. 4) | 145–165 |
|  | 3' Primer | ATGTATGCCGGTGCTGGCTATATTT (SEQ ID NO. 5) | 451–477 |
|  | Probe | TCAGGATGCGGTCGCCCTCCAC (SEQ ID NO. 6) | 301–322 |
| human GAPDH | 5' Primer | CCCATCACCATCTTCCAGGAG (SEQ ID NO. 7) | 211–231 |
|  | 3' Primer | GTTCTCATGGATGACCTTGGC (SEQ ID NO. 8) | 475–495 |
|  | Probe | CTAAGCAGTTGGTGGTGCAGG (SEQ ID NO. 9) | 446–466 |
| human. platelet 12-LO | 5' Primer | GATGATCTACCTCCAAATATG (SEQ ID NO. 10) | 472–492 |
|  | 3' Primer | CTGGCCCCAGAAGATCTGATC (SEQ ID NO. 11) | 610–630 |
|  | Probe | GTTTGAGGGCCATCTCCAGAGC (SEQ ID NO. 12) | 544–565 |

4. Amplification of Reverse Transcribed RNA Using the Polymerase Chain Reaction (RT-PCR)

Total RNA from cultured HSMC, HAEC and fresh MO was extracted with guanidiumthiocyanate-phenol-chloroform using RNAzol (Cinna/Biotecx Laboratories International Inc., Texas). Some RNA samples were treated by RNAse-free DNAse. 3 microgram of total RNA was mixed with the PCR buffer (10 mmol/L Tris-HCl, pH 8.3, 50 mmol/L KCl, 1.5 mmol/L $MgCl_2$, and 0.001% gelatin), 200 μmol/L of each of the four deoxynucleotide triphosphates, 25 pmol each of 5'- and 3'-primers, 2 U Avian Myeloblastosis Virus reverse transcriptase (20 U/μl; Life Sciences, St. Petersburg, Fla.), and 2.5 U Taq polymerase (Perkin Elmer Cetus, Norwalk, Conn.) in a final vol of 50 μl. In some reactions, 5 pmol of each 5'- and 3'-primer of $β_2$ macroglobulin or GAPDH were added as an internal standard. The samples were placed in a thermal cycler at 37° C. for eight minutes for the RT reaction to proceed. Then conditions used for PCR were a denaturation step at 94° C. for one-minute, annealing at 50° C. for two minutes, and extension at 72° C. for two minutes for 20–40 cycles. Blank reactions with no RNA template were carried out through the RT and PCR steps. The human 15-LO cDNA, porcine leukocyte 12-LO cDNA, and human platelet 12-LO cDNA amplifications were carried out by mixing 2–5 ng cDNA plasmid in a 50 μl vol containing 200 μmol/L of each of the four deoxynucleotide trisphosphates, 25 pmole 5'- and 3'-primers, and 2.5 U Taq polymerase. The conditions for PCR were the same as described before.

5. Gel Analysis and Blot Hybridization

20 μl aliquots of the PCR products were subjected to electrophoresis in a 1.8% agarose gel in Tris acetate-EDTA buffer. After staining with ethidium bromide and photographing, the gel was transferred onto a Zeta-probe membrane (Bio-Rad, Richmond, Calif.) by capillary blotting. The oligonucleotides used as probes were labeled at the 5'-end using [$γ^{32}$P]ATP and T4 polynucleotide kinase (New England Biolabs, Beverly, Mass.) and hybridized with membrane overnight in 6× SSC (1× SSC contains 0.15 mol/L NaCl, 0.015 mol/L sodium citrate), 0.5% non-fat dried milk and 7% SDS at 42° C. Membranes were washed once in 6× SSC at room temperature for 15 minutes and then once at 60° C. for 15 minutes. The washing conditions were worked out to distinguish between the PCR products of human 15-LO from those of porcine leukocyte 12-LO (3). The filters were exposed to Kodak x-ray film (Eastman Kodak Co., Rochester, N.Y.) with an intensifying screen at −70° C. Blots were quantitated using a computerized video densitometer.

6. Western Immunoblotting

Cells pellets were lysed in lysis buffer containing PBS (pH 7.3), 1% Triton X-100, 1 mmol/L phenylmethylsulfonyl fluoride, 50 μmol/L leupeptin, and 0.1% sodium dodecyl sulfate (SDS). Lysates were centrifuged at 10,000×g for 10 minutes. An aliquot of the supernatant (cytosol) was saved for protein estimation and the remainder saved at −70° C. for Western Blot analysis.

SDS polyacrylamide gel electrophoresis (10% running gel, 4% stacking gel) was performed according to the method of Laemmli (24). For Western blotting, gels were equilibrated in transfer buffer (35 mmol/L Tris base, 192 mmol/L glycine, and 20% methanol, pH 8.3) and then transferred to nitrocellulose (Hybond, Amersham, Arlington Heights, Ill.) as described by Towbin et al. (25), in a semidry polyblot apparatus (American Bionetics, Inc., Emeryville, Calif.) for 40 minutes. The nonspecific sites were blocked with PBS containing 10% of FCS at 4° C. overnight. The membranes were then washed twice with PBST (PBS+ 0.05% Tween-20) and incubated with primary antibody in PBST containing 1% BSA and 20% (vol/vol) FCS for 2 hours at room temperature. A polyclonal antibody against porcine 12-LO peptide with the sequence of amino acids 646–662 of the porcine leukocyte 12-LO sequence (14) was used. This antiserum was used at 1:100 dilution. In some studies, a polyclonal antibody against human 15-LO kindly provided by Dr. E. Sigal (Syntex Co., Palo Alto, Calif.) was used. The washed membranes were then incubated for 1 hour with second antibody (goat antirabbit) conjugated with alkaline phosphatase (1:5000; Promega, Madison, Wis.). Detection was either by color development using substrate mixture (Nitroblue tetrazoleum and 5-bromo-4-chloro-3-indolyl phosphate from Promega) or by chemiluminescence using CSPD substrate and the Western-Light Chemiluminscent detection system (Tropix, Inc., Bedford, Mass.). Nonspecific binding was evaluated using normal rabbit serum. Western blots were quantitated using a computerized video densitometer (Applied Imagining, Santa Clara, Calif.; Lynx DNA vision) and values expressed as arbitrary absorbance units.

7. Measurement of 12-LO Products

These assays were performed using previously published methods (10,11). Briefly, 12- and 15-HETE are extracted from supernatants and cells on C18 mini columns (Analytichem International, CA) and measured using our validated reverse phase gradient HPLC and (RIA) methods.

8. Measurement of Lipoxygenase Activity in HSMC

Confluent HSMC were placed in media plus 10% FCS 24 hours prior to the experiment. The cells were harvested, washed, suspended in 1 ml Tris-HCl buffer (25 mmol/L, pH 7.7) and then sonicated on ice. The assay mixture contained in 1.0 ml, 800 $\mu$l enzyme (sonicate), 100 $\mu$l $CaCl_2$ (1.5 mmol/L) and 50 $\mu$l glutathione (0.5 mmol/L). An enzyme blank was run simultaneously. The reaction was started at 37° C. with 50 $\mu$l sodium arachidonate (160 $\mu$mol/L Nu Check Prep, Elysain, Minn.) or 0.25 $\mu Ci^{14}[C]$ linoleic acid (New England Nuclear). After 10 minutes incubation, the reaction was stopped with 2 ml isopropanol/1.2% acetic acid followed by 2 ml chloroform. The lower organic layer was filtered and subjected to HPLC to detect HODEs or HETEs using applicants' gradient reverse phase HPLC system (10, 11). 12-HETE peak was identified by UV detection at 237 nM and co-migration with authentic standard (retention time 18.3 minutes). Peak heights were quantitated using a Shimazu CR5A integrator. For the identification of radioactive linoleic acid metabolites, $^{14}[C]$ HODEs, radioactivity in the fraction co-migrating with the same retention time as the authentic cold HODEs was quantitated. In this HPLC system, both 9- and 13-HODE have the same retention time (17.9 minutes).

9. Immunohistochemistry

The immunohistochemical method used has been previously described (26). Briefly, five micron sections of tissue samples derived from a lower extremity amputation for peripheral vascular disease or a coronary artery showing an atherosclerotic plaque were mounted on Silane (3-Aminoprypyltriethoxysilane, Sigma, St. Louis, Mo.) coated slides and dried overnight at 60° C. After deparaffination and dehydration they were placed in a 10 mmol/L citrate buffer solution (pH 6.0) and boiled in a microwave oven for two periods of 5 minutes each. After cooling, the sections were twice washed in distilled water. Following a 20 minute incubation in 1% hydrogen peroxide/methanol, the slides were washed twice in distilled water and twice in phosphate buffered saline (PBS). This was followed by blocking with normal horse serum 1:20 in PBS (Vector Labs). After decanting, the sections were covered with rabbit peptide anti-leukocyte 12-lipoxygenase antisera at 1:1000 dilution and incubated overnight in a humid chamber at room temperature. After two washes in PBS the slides were incubated for 40 minutes with biotinylated anti-rabbit IgG (Elite kit, Vector Labs, Burlingame, Calif.) at 1:600 dilution. After two additional washes in PBS the sections were incubated in AB complex (Elite kit, Vector Labs) at 1:200 dilution for another 40 minutes. The sections were then exposed to a Diamino benzidine solution for 7 minutes for color development. After two additional washes, the color was enhanced by incubating the sections in 1% copper sulfate for 5 minutes. All the steps were performed using an automatic stainer (Techmate 1000, Biotek Solutions, Santa Barbara, Calif.). Sections from the peripheral vessel were washed again and lightly counter stained in 6% Mayer's hematoxylin, washed, dehydrated and coverslipped. The sections form the coronary artery were not counter stained. Control slides were prepared by substituting anti-12-lipoxygenase with pre-immune rabbit serum at the same concentration.

10. Data Analysis

Immunoblots and autoradiograms were analyzed using a computer driven densitometer (Applied Imaging, Santa Clara, Calif.; Lynx DNA Vision). Data shown is representative of two to three experiments. Data generated from AII treatment of HSMC for 12-HETE synthesis was analyzed using ANOVA for multiple samples using a statistical package on a Macintosh computer system. Data is presented as mean±SE.

Results of Experimental Procedures

Expression of a Leukocyte Type of 12-LO mRNA in HAEC, HSMC, and MO

The expression of 12-LO mRNA in HAEC, HSMC and MO was evaluated using a specific RT-PCR method since the level of detection was below the sensitivity of Northern analysis. FIG. 1A shows expression of leukocyte 12-LO mRNA in normal HAEC, HSMC, and MO using a method highly specific for this form of 12-LO mRNA. The appropriate 333 base pair band was seen in all three cell types.

FIG. 1B demonstrates RT-PCR analysis of human 15-LO mRNA expression from the same RNA. These results reveal no evidence for a band characteristic of human 15-LO. In a separate experiment, RNA from HAEC, HSMC, and MO was amplified and probed for the platelet type 12-LO RNA. No evidence for a human platelet 12-LO expression was found (data not shown).

Expression of hl 12-LO Protein in HAEC, HSMC and MO

To investigate whether a leukocyte type of 12-LO enzyme was expressed in vascular and circulating MO, the 10,000×g supernatant proteins were electrophoresed and subjected to Western analysis using a polyclonal peptide antibody derived from a sequence in the porcine leukocyte type of 12-LO that is homologous to the sequence of 12-LO found in human adrenal glomerulose. This antibody has previously been shown to lack cross reactivity to the platelet form of 12-LO and successfully demonstrated the presence of a leukocyte type 12-LO in human adrenal cells (3). FIG. 2 demonstrates a major 72 kD band from Western analysis in HSMC, HAEC, and MO. Western analysis similarly performed using a polyclonal antibody directed against the human 15-LO protein did not demonstrate a band in the expected molecular weight form these cells (data not shown). HAEC and MO produced 12-S-HETE as reflected by HPLC and RIA analysis (HAEC 2386, MO 820 pg/$10^6$ cells) Results for HSMC are detailed below.

Therefore, HSMC, HAEC and MO appear to express a 12-LO protein which is similar to the leukocyte type of 12-LO found in porcine tissues and human adrenal glomerulose.

Figure 3A:
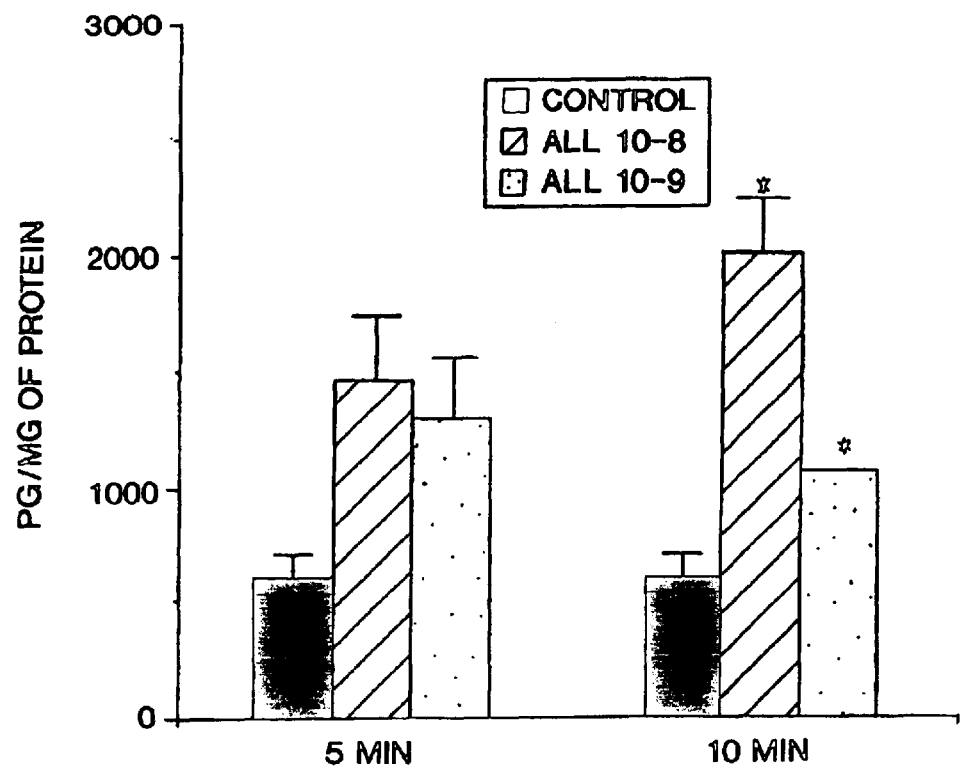
Figure 3B:
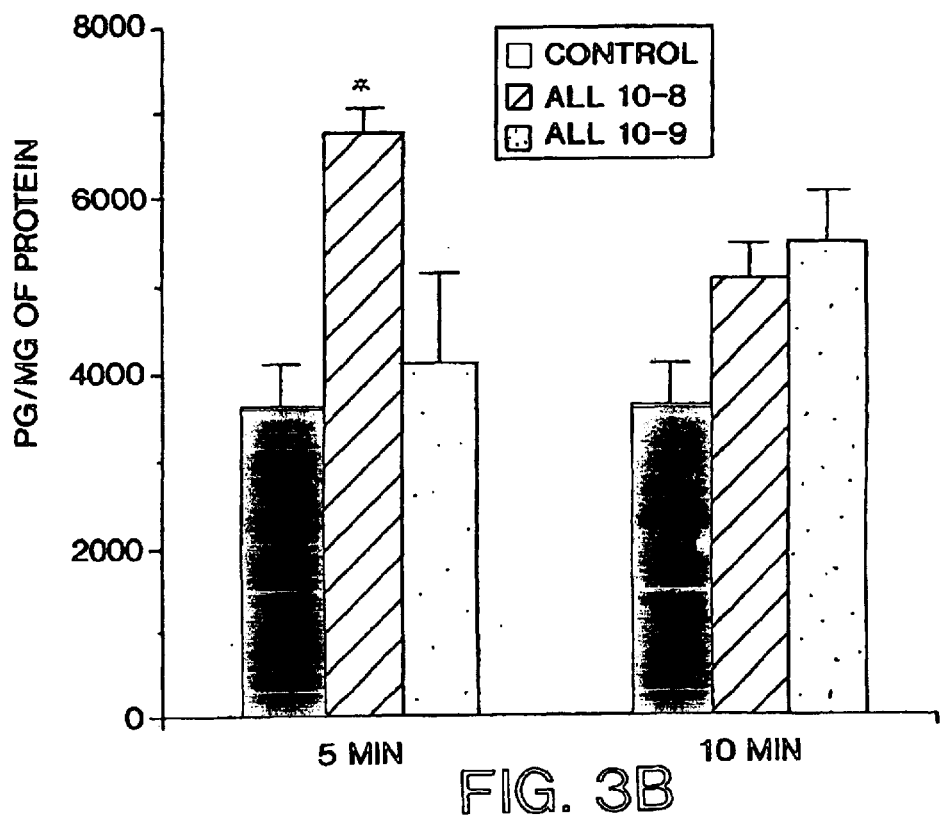

Effect of AII on 12-LO Activity and Expression in HSMC and Certain Other Tissues Another major aspect of this invention is the discovery that AII increases the activity and expression of 12-LO mRNA and protein in HSMC. FIG. 3A shows that 5 minute incubation of HSMC with AII at the concentrations of $10^{-8}$ mol/L and $10^{-9}$ mol/L in serum free media stimulates the release of 12-HETE (control: 599±105; AII $10^{-8}$M: 1467±277; AII $10^{-9}$ mol/L: 1296±262 pg per mg of protein). Ten minute incubations with AII also significantly simulated the release of 12-HETE at the concentration of $10^{-8}$ mol/L. AII significantly also increased cell-associated 12-HETE levels in HSMC (FIG. 3B). In other studies, it was found that 12-HETE levels in response to AII could be reduced by the LO inhibitor baicalein $10^{-5}$ mol/L (data not shown).

Figure 4A:
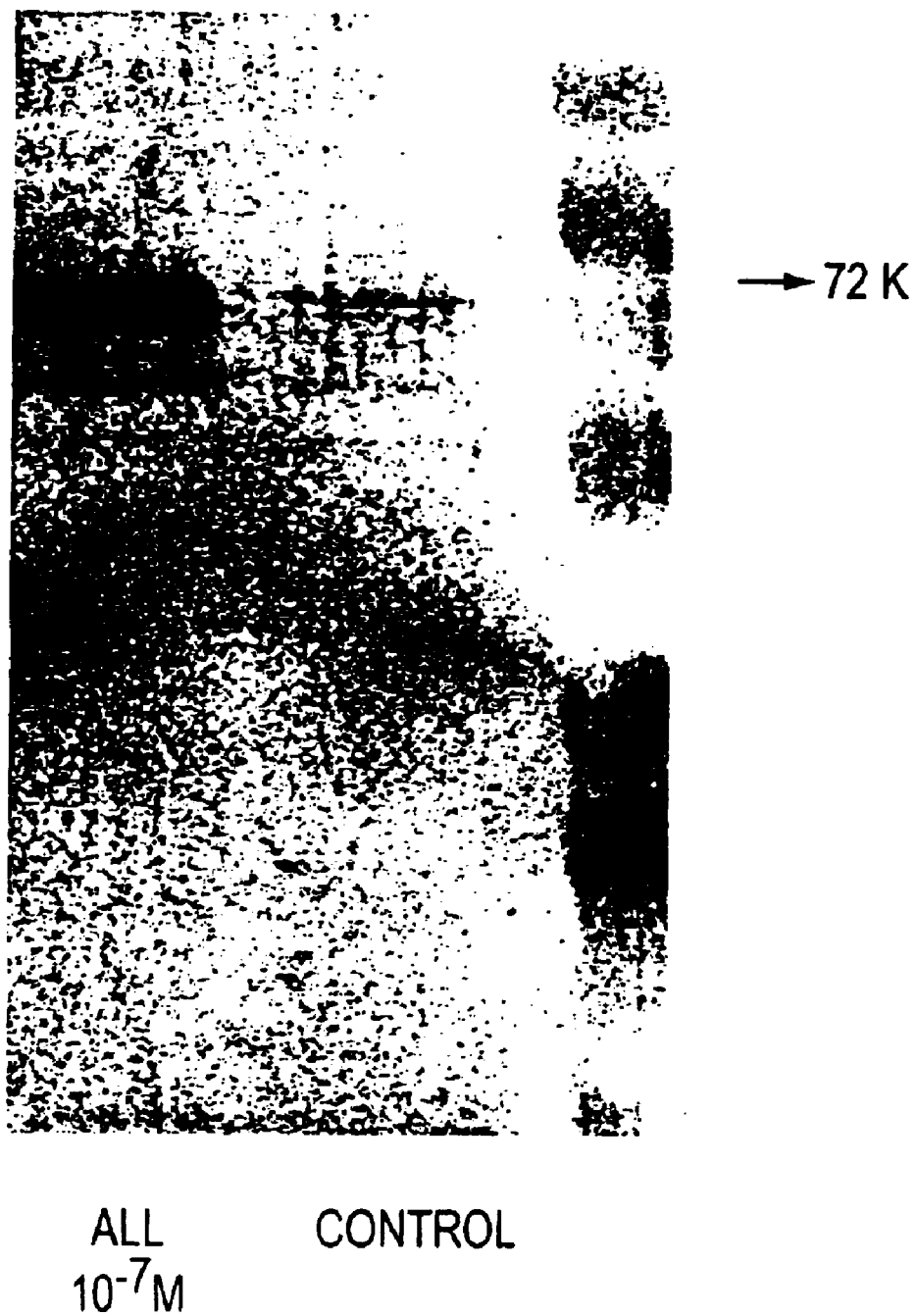
Figure 4B:
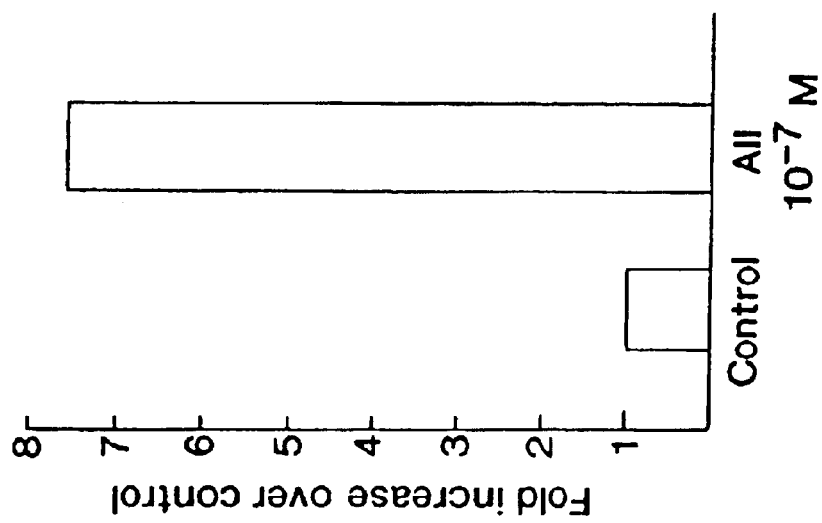

To examine whether AII induces the 12-LO enzyme expression in HSMC, cells were treated with AII at the concentration of 2×10$^{-7}$ mol/L for 24 or 48 hours. The 12-LO protein was identified by Western immunoblotting using a specific antibody to purified leukocyte type 12-LO or a peptide antibody derived from known sequences present in the human leukocyte type of 12-LO. A distinct band was detected with a molecular weight of nearly 72 kD which is the reported molecular weight of the porcine leukocyte-type of 12-LO (FIG. 4). A 24 hour incubation of HSMC with AII in serum free media induced nearly a seven fold increase in 12-LO protein expression (FIG. 4). In other experiments, AII was added for 48 hours also induced 12-LO expression 4–7 fold (data not shown).

Figure 5A:
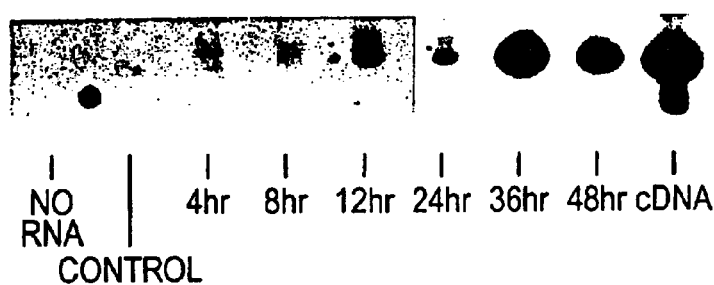
Figure 5B:
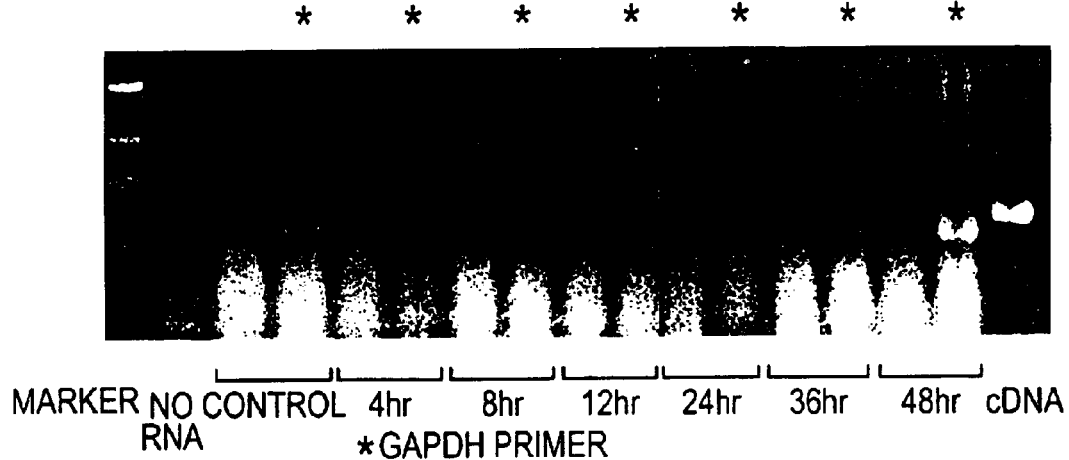

In order to evaluate the specific expression and regulation of 12-LO mRNA in HSMC, applicants used a RT-PCR assay that exclusively amplifies the leucocyte type of 12-LO. The size of the PCR amplified fragment is 333 bp for both 12- and 15-LO. Therefore, specific conditions were used to distinguish leukocyte type 12-LO and human 15-LO by increasing stringency and raising washing temperature to 60° C. FIG. 5A shows a Southern blot analysis of RT-PCR amplified products from HSMC serum-deprived for 24 hours and then treated for the indicated times with AII 10$^{-7}$ mol/L. In this experiment, very low basal expression of 12-LO is seen. However, in other experiments in cells from various other donors, basal 12-LO expression is detectable with PCR at 20–30 cycles. AII induces 12-LO mRNA expression starting at the 12 hour incubation time and the maximum induction is shown at 36 hour incubation of cells with AII. FIG. 5B shows the ethidium bromide stained agarose gel showing the amplification of GAPDH as an internal marker. When PCR conditions were used that were specific for either the platelet type 12-LO or human 15-LO no specific RNA band was detected (data not shown). Therefore, basal serum deprived HSMC show low expression of a leukocyte type 12-LO which is markedly upregulated by AII.

The leukocyte type of 12-LO, unlike the platelet form can also metabolize linoleic acid. Therefore, applicants evaluated whether the HSMC could form 13-HODE, the linoleic acid metabolite of LO action in addition to 12-HETE, the product of arachidonic acid metabolism. The accomplish this, applicants performed separate experiments in which the appropriate cytosolic fractions of HSM were treated with either C$^{14}$ linoleic acid or cold arachidonic acid and the LO products of the HSMC were analyzed by a gradient reverse phase HPLC system. Cells labelled with cold arachidonic acid showed HPLC peaks co-migrating with 12-HETE. The peak height in the cell blank sample was 1.5 cm which increased to ⅗ cm in the HSMC sonicate. Cells incubated with C$^{14}$ linoleic acid also produced 13-HODE (695 counts per minute blank to 1038 counts HSMC sonicate).

Figure 6A:
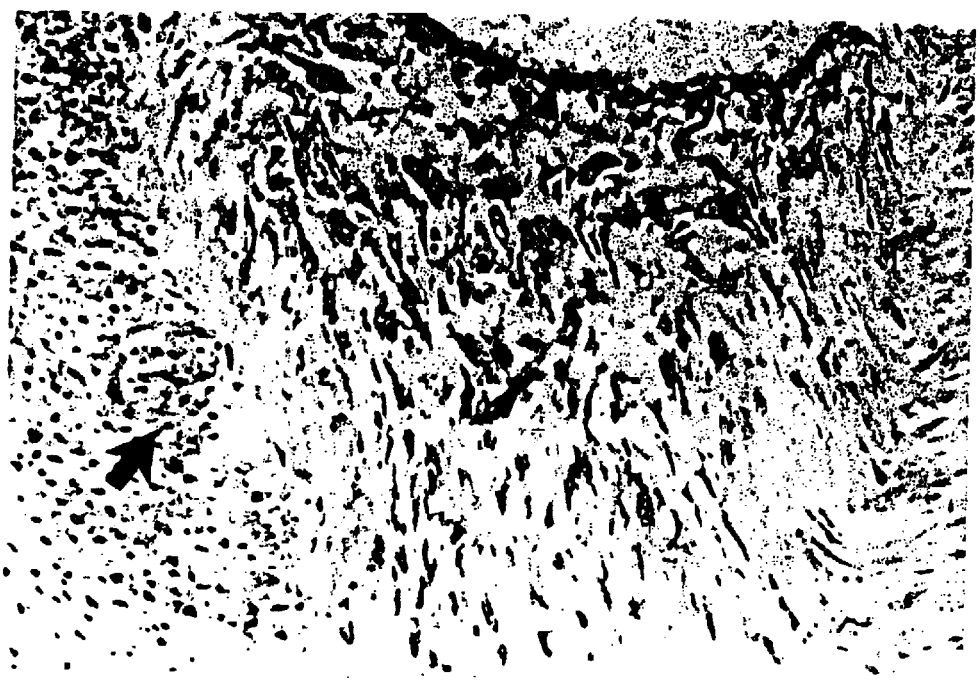
Figure 6B:
Figure 7A:
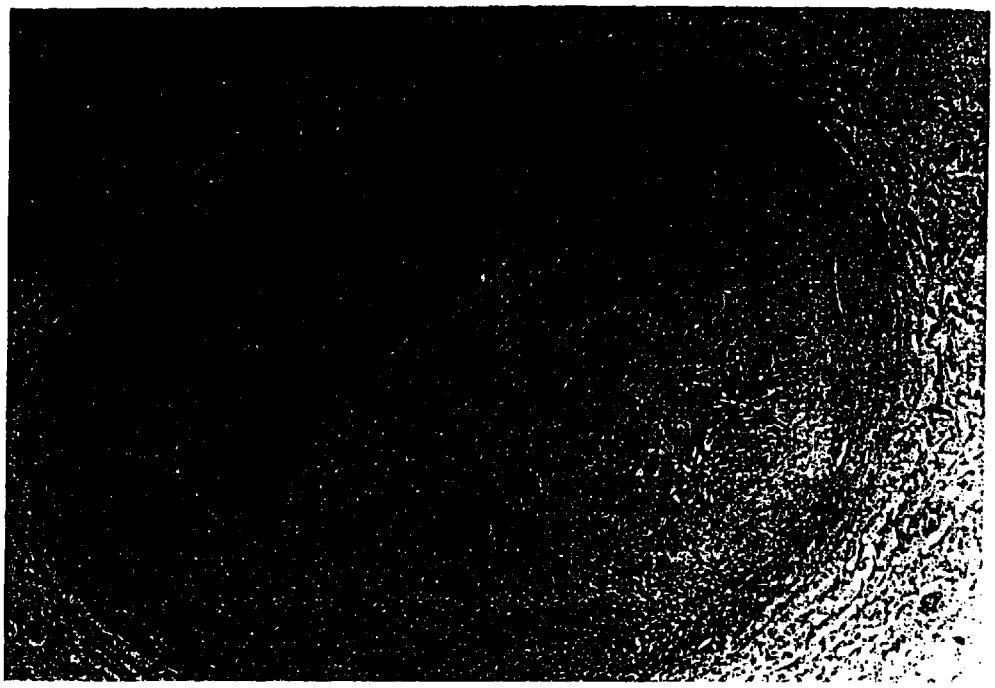
Figure 7B:
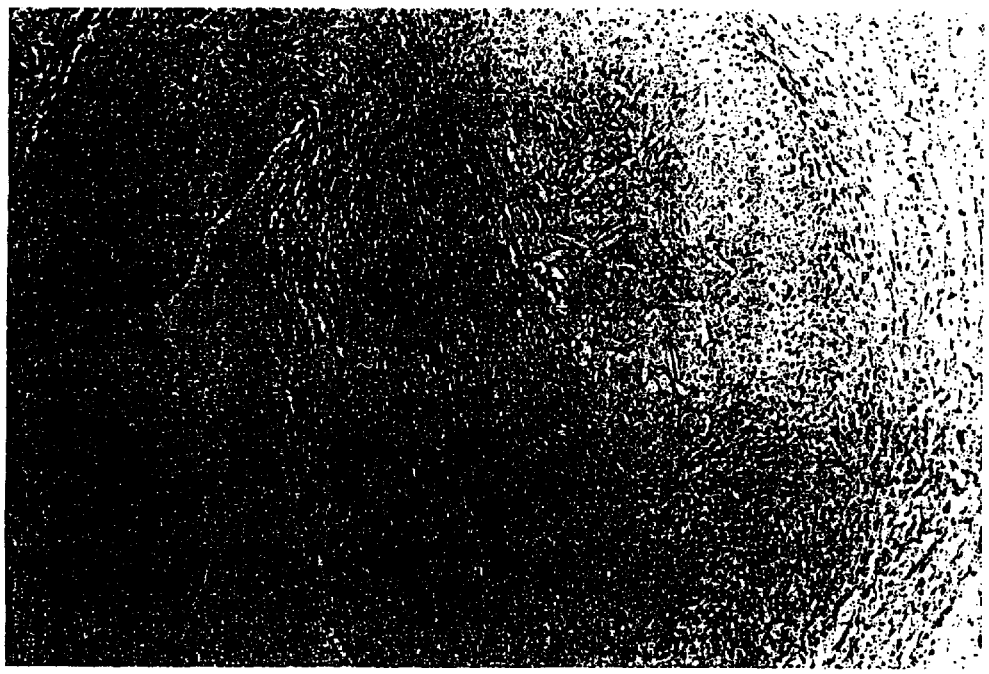

To evaluate whether a leukocyte type of 12-LO is present in atherosclerotic lesions, immunohistochemistry was performed using the peptide anti-leukocyte type 12-LO antibody. FIG. 6A represents a high power section derived from a lower extremity amputation specimen from a patient with peripheral vascular disease. Specific cytoplasmic staining for leukocyte type of 12-LO is evident in both the endothelial and smooth muscle layers of this lesion. The neointimal area also demonstrates staining for leukocyte type 12-LO. FIG. 6B represents a high power section from the same lesion stained with pre-immune antisera. This section demonstrates minimal background staining suggesting that the staining for leukocyte type 12-LO in FIG. 6A is specific. FIG. 7 is a representative section from a left human coronary artery showing an advanced atherosclerotic lesion. FIG. 7A shows definite staining for 12-LO protein in the smooth muscle and adventitial areas as well as endothelial cells. FIG. 7B represents immunohistochemistry with the pre-immune antisera showing very little background staining with this antibody.

These results demonstrate that a 12-LO RNA and protein similar to that found in porcine leukocytes and human adrenal glomerulose (3) is also expressed in human vascular cells and circulating monocytes. Several approaches were utilized in this current investigation to support this conclusion. First, a peptide antibody derived from a sequence common to the porcine and human form of leukocyte type of 12-LO revealed a characteristic 72 kD band in HSMC, HAEC and MO lysates. This antibody does not cross react with the platelet form of 12-LO but has partial cross reactivity with human 15-LO (3). Second, a highly specific RT-PCR procedure was used to detect 12-LO mRNA in these cell types. In a previous study, it was demonstrated using this technique that a leukocyte type of 12-LO was the exclusive type of 12-LO seen in human adrenal glomerulose and U937 cells (3). In the present study, a specific 333 base pair amplified mRNA product was found in unstimulated HSMC, HAEC and MO when appropriate leukocyte type 12-LO primers and probe were utilized. Thirdly, in all three cell types, the 12-LO product 12-S-HETE was formed as reflected by HPLC and specific RIA. The cytosol from HSMC reacted with both arachidonic and linoleic acid to produce either 12-HETE or 13-HODE respectively. This reaction is characteristic of a leukocyte type of 12-LO and not the platelet 12-LO which only reacts with arachidonic acid to produce 12-HETE.

The human 15-LO originally cloned from the reticulocyte and found in human trachea is highly homologous (86% sequence homology) to the porcine leukocyte type of 12-LO (14). The PCR technique utilized here can distinguish between the leukocyte 12-LO and the 15-LO (3). The specificity of this approach was demonstrated using the 12-LO and 15-LO cDNA as templates for amplification (3). Therefore, the Southern blot hybridization using the leukocyte 12-LO probe provides the strongest evidence that the band seen reflects a 12-LO and not a 15-LO amplified product. These results are in agreement with previous studies showing no detectable 15-LO mRNA in basal or stimulated human endothelial or non-stimulated mononuclear cells (27). However, 15-LO mRNA and protein has been found in macrophage rich areas of atherosclerotic vascular lesions and in IL-4 stimulated monocytes (28) suggesting that 15-LO can play a role in advanced atherosclerotic and immune mediated vascular disease.

Increasing evidence also suggests that a 12-LO enzyme plays an important role in AII-induced actions in several additional tissues. Studies suggest that the 12-LO pathway of arachidonic acid can mediate AII-induced aldosterone synthesis in rat and human adrenal glomerulose cells (11, 12). Furthermore, recent data indicates that AII-induced adrenal cell proliferation is mediated at least in part by activation of a 12-LO enzyme. Additional studies in the rat have implicated the 12-LO pathway in the vasoconstrictive and renin-inhibitory actions of AII (29). The aorta has the capacity to produce LO products including 12 and 15-HETE (30). Recent data has revealed that both AII and high glucose can up-regulate the leukocyte type of 12-LO in cultured porcine aortic smooth muscle cells (31).

AII has major effects on vascular smooth muscle cell growth in vitro and in vivo (1, 7, 32–34). In a recent report, it was found that a relatively selective 12-LO inhibitor but not a cycloxygenase inhibitor could completely prevent AII-induced hypertrophic responses in cultured porcine vascular smooth muscle cells (35). Furthermore, 12-HETE induced similar increases in protein and fibronectin content of these vascular smooth muscle cells as AII (36). The 12-LO pathway and its product 12-HETE has also been implicated in vascular smooth muscle cell migration (9). 12-HETE at concentrations as low as $10^{-12}$M have been shown to lead to smooth muscle cell migration. Additional studies have demonstrated that 12-LO products can activate specific isoforms of protein kinase C and oncogenzes including ras, c-fos and jun (36–38).

Increased 12-LO activity and expression by AII may therefore be a previously unrecognized mechanism for AII-induced hypertensive and atherosclerotic vascular disease in humans. Accordingly, another important aspect of this invention entails blockade of the 12-LO pathway as a novel therapeutic modality to reduce AII related cardiovascular disease.

The 12-LO pathway in the human vascular wall and monocytes may participate in other mechanisms related to the development or progression of atherosclerotic vascular disease. Recent evidence has implicated a LO pathway in oxidative modification of LDL in the vascular wall (39–41). It is now clear that HAEC, HSMC or monocytes have the capacity to convert native LDL to minimally modified LDL which has a greater atherosclerotic potential. Of interest is the data showing that cholesterol loading of macrophages primarily leads to increased production of 12-HETE (42). A recent report has now demonstrated that both the leukocyte type of 12-LO and 15-LO can similarly oxidize lipoproteins (42). Interestingly, this same report showed a lack of ability of the platelet 12-LO to oxidize lipoproteins.

To provide additional evidence for the presence and localization of a leukocyte 12-LO in human vessels, immunohistochemical analyses of two atherosclerotic lesions were performed. The results provide immunohistochemical evidence that a leukocyte type of 12-LO is particularly expressed in the endothelial and smooth muscle cells of an atherosclerotic lesion supporting a potential role of this pathway in the early progression of atherosclerotic vascular disease. Previous studies have shown that vascular tissues and monocytes have LO activity (42–44).

Pathways by which AII and 12-HETE Function

It has now been discovered that AII and 12-HETE effect changes in cells by stimulating mitogen activated protein (MAP) kinase activity. Specifically, AII and 12-HETE function by activating transcriptional activity of fos via ERK (extracellular regulated kinases) (e.g., ERK 1 ($P44^{MAPK}$), ERK 2 ($P42^{MAPK}$) and ERK3 ($P62^{MAPK}$)), by activating jun via JNK (cJun kinases or stress activated kinases) and/or by activating JAK (Janus kinases e.g., JAK1 and JAK2). More specifically, AII and 12-HETE activate P-21 activated kinase (PAK), which has been implicated as a key upstream signal for JNK activation.

Experimental Procedures

ERK Activity:

ERK activity was evaluated by the substrate-SDS-polyacrylamide gel method described in Anal. Biochem., 183:139–143 (1989). Confluent cells in 100 mM dishes were made quiescent in serum-free medium and then treated with agonists for various time periods. The cells were then lysed in lysis buffer (1% NP40, 1% sodium deoxycholate, 0.1% SDS, 100 mM NaCl, 50 mM Tris, 10 mM EDTA, 1 mM EGTA, aprotinin, 100 mg/ml leupeptin, 0.1 mM PMSF and 1 mM sodium orthovanadate, pH 7.4). Lysates were centrifuged to pellet nuclei and the cell extracts (15–20 mg protein) were subjected to electrophoresis on SDS-polyacrylamide gels (10%) containing myelin basic protein (0.5 mg/ml) as an ERK substrate. The SDS was then washed, followed by denaturation, renaturation and protein phosphorylation on the gel with [$^{32}$P] ATP.

JNK Activity:

The plasmid pGEX-cJun 1/79 (Dept. Pharmacol. UCSD, La Jolla) is a GST-cJun (1–79) expression vector encoding amino acids (1–79) of cJun. The GST fusion protein expression vector was transformed into E. Coli. Protein was induced with 0.1 mM IPTG and purified by affinity binding to glutathione-agarose beads. Unstimulated or stimulated cells were lysed into WCEB (25 mM HEPES, pH 7.7, 03.M Nacl, 15 mM $MgCl_2$, 02.mM EDTA and 0.1% triton X-100). About 50 μg protein extract was incubated with GST-cJun+ GSH agarose overnight at 4° C. Phosphorylation was carried out at 30° C. for 20 minutes in the presence of 20 mM HEPES, pH 7.5, 20 mM b-glycerophosphate, 10 mM p-nitrophenolphosphate, 10 mM $MgCl_2$, 10 mM DDT, 50 μg $Na_3VO_4$, 20 μM ATP (cold) and about 0.5 μl of new gamma $^{32}$P-ATP. After boiling with electrophoresis sample buffer, the supernatants were analyzed on 12% SDS-PAGE. JNK activity was also measured by immunoprecipitation method using an anti-JNK antibody (Parmingen Co., San Diego) and then activities were measured using 2 μg of GST-cJun (1–79) as substrate as described in Cell, 81:1147–1157 (1995).

PAK Activity:

Cell lysis and PAK activity measurement were performed as described in Science, 269:221–223 (1995). Cells were lysed on ice in 50 mM Tris-HCl, 150 mM NaCl, 5 mM EGTA, 50 mM NaF, 10 mM Na pyrophosphate, 1% NP-40, 2.5% glycerol, and 1 mM $Na_3VO_4$ (pH 7.5), containing protease inhibitors PMSF, leupeptin and aprotinin. Cell were centrifuged for 10 minutes at 1000 g. For immunoprecipitation, the supernatants were incubated with anti-PAK1 or anti-PAK2 antibody (1:25) (Dept. Immuno. & Cell Biology, Scripps Res. Instit., La Jolla, Calif.) for 2 hours at 4° C. followed by incubation with 60 μl of 1:1 protein A beads for 60 minutes, then 5×1.0 ml lysis buffer washes and 2 washes with kinase buffer (50 mM HEPES, pH 7.5, 10 mM $MgCl_2$ 0.2 mM dithiothreitol, 2 μg myelin basic protein and 14 Mμ [r-$^{32}$P] ATP) for 20 minutes at 30° C. The reaction was stopped with SDS sample buffer, and results were visualized by SDS-PAGE and autoradiography.

Results

It has been discovered that the administration of AII results in biphasic activation of MAP kinase (all of the MAP kinase experiments were conducted in CHO-AT1a cells— AII receptor AT1a cDNA transfected Chinese hamster ovary cells). It has been found that AII ($10^{-7}$M) induces a biphasic stimulation of ERK activity with a first peak of activity at 5 minutes (2–6 fold) and a later peak at 3–4.5 hours (1.5–3 fold) as well as a stimulation of JNK activity which peaks at 30 minutes and remains sustained for 1 hour. It has also been found that AII ($10^{-7}$M) induces stimulation of PAK with one major peak at 30 minutes (5 fold).

It has also been discovered that 12-HETE ($10^{-7}$M) induces a biphasic stimulation of ERK activity with a first peak at 5 minutes and a second peak at 3–4.5 hours as well as a biphasic stimulation of JNK activity with peaks at 30 minutes (2–3 fold) and 3 hours (2.5–5 fold). It has been found that 12-HETE stimulates JNK activity at concentrations as low as $10^{-9}$M, as shown in FIG. 29.

It has further been discovered that 12-HETE induces stimulation of JAK activity. CHO-AT$_{1a}$ cells were treated with 12-HETE ($10^{-7}$M) for 10 hours, immunoprecipitated with a phosphotyrosine antibody and immunoblotted using specific JAK1 and JAK2 antibodies. As can be seen in FIG. 30, 12-HETE increased JAK activity.

Finally, it has been discovered that 12-LO inhibitors (e.g., CDC and baicalein) dose-dependently reduce AII- and 12-HETE-induced mitogenic activities. Thus, the administration of a 12-LO inhibitor decreases AII- and/or 12-HETE-induced MAP kinase activity, thereby decreasing the effects which AII and/or 12-HETE have on cell growth and development.

Consistent with this data, one aspect of the present invention entails therapy for AII- or 12-HETE-induced disease in humans which includes reducing ERK, JNK and/or JAK activity via the administration of a 12-LO inhibitor. While not wishing to be bound by a particular theory, it is believed that 12-HETE increases MAP kinase activity through upregulation of 12-HETE receptors. Thus, therapy for AII- or 12-HETE-induced disease also includes reducing mitogenic activity via the administration of a 12-HETE receptor antagonist such as, for example, DuP654.

Inhibition of the 12-LO Pathway

The utilization of various pharmacologic, antisense or ribozyme methods to reduce leukocyte type 12-LO activity is described in application PCT/US94/00089. Panaxynol, a polyacetylene compound isolated from ginseng has been identified as a relatively selective inhibitor of leukocyte 12-LO (55) and is useful for the purpose of this invention.

Role of the 12-LO Pathway in Breast Cancer Cell Growth

Example V of application PCT/US94/00089 indicates that blockage of the 12-LO pathway provides useful human breast cancer therapy. A further evaluation of the regulation of 12-LO activity and expression in breast cancer cells and tissues confirms that proliferation of breast cancer tissue is inhibited by 12-LO inhibitors. Specifically, leukocyte-type 12-LO mRNA expression was studied by a specific reverse transcriptase PCR method in matched normal uninvolved and cancer involved breast tissue RNA samples from six patients. It was observed that in each of the six patients, the cancer involved section showed a much higher level of 12-LO mRNA (340 bp PCR product) than the corresponding normal section (3–6 fold higher after normalization to the internal control for PCR, GADPH mRNA 284 bp). 12-LO mRNA levels were also 7- and 11-fold greater in two breast cancer cell lines, MCF-7 and COH-BR1 compared to the normal breast epithelial cell line, MCF-10F. In addition, the proliferation of MCF-7 cells was significantly inhibited by three LO inhibitors, baicalein (10 $\mu$M), CDC ($10^{-5}$M) and NDGA (30 $\mu$M), but not by a cyclooxygenase inhibitor, ibuprofen ($10^{-5}$M). Treatment of serum-starved MCF-7 cells with EGF for four hours lead to a dose dependent increase in the formation of the 12-LO product, 12-HETE (basal 257±10 pg/$10^6$ cells; EGF 50 ng/ml 462±15 pg; EGF 100 ng/ml 593±46 pg, both p<0.001 vs basal). EGF (50 ng/ml) also led to a marked increase in the levels of the 12-LO protein (72 kD) as well as 12-LO mRNA at 24 hours. Hence, activation of the 12-LO pathway appears to play a key role in basal and EGF-induced breast cancer cell growth and development.

Role of the 12-LO Pathway in the Action of Estrogen in Breast Cancer

It has now been discovered that estrogen, which has been linked to breast cancer cell growth and development, plays a role in activating the 12-LO pathway in breast cancer cells.

Treatment of cells from the estrogen receptor positive breast cancer cell line, MCF-7, with 17β-estradiol for 4 hours in a defined serum-free and phenol red-free medium led to a dose-dependent increase in the levels of cell associated 12-LO product 12-hydroxyeicosatetraenoic acid (12-HETE) (Basal 161±29 pg/$10^6$ cells; 17β-estradiol, 5 nM 784±150 pg; 17β-estradiol, 10 nM 1056±187 pg; both p<0.001 vs basal). This stimulatory effect of 17β-estradiol on 12-HETE was not observed in the estrogen receptor negative cell line MDA-MB-231. Treatment of MCF-7 cells with estrogen for 22 hours also caused a dose-dependent increase in the expression of the leukocyte-type 12-LO protein as examined by immunoblotting with a 12-LO peptide antibody (2.1-fold and 3-fold increase over basal at 1 nM and 10 nM 17β-Estradiol respectively). Thus, 17β-estradiol increased 12-LO activity and expression in MCF-7 cells. Hence, activation of the 12-LO pathway appears to play a key role in estrogen-induced breast cancer cell growth and development.

Consistent with this data, one aspect of this invention entails therapy to reduce breast cancer cell growth and development through inhibition of the 12-LO pathway. Such 12-LO pathway inhibition would, inter alia, reduce the effect estrogen has on breast cancer cell growth and development.

Role of the 12-LO Pathway in The Formation of VEGF

Applicants have also discovered that the 12-LO pathway plays a role in the formation of vascular endothelial growth factor (VEGF). VEGF is an endothelial cell-specific mitogen which increases vascular permeability and monocyte migration. VEGF appears to be a major angiogenic factor for many types of cancer, including breast and lung cancer. Further VEGF has been linked to the development of proliferative diabetic retinopathy as well as accelerated vascular disease often associated with diabetes.

Figure 8:
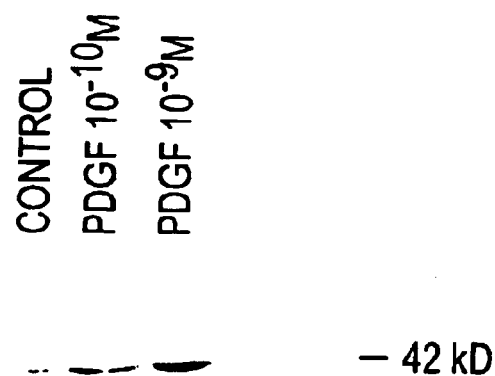
FIG. 8 is an immunoblot illustrating the dose-dependent effect of PDGF on UEGF expression in MCF-7 cells.
Figure 9:
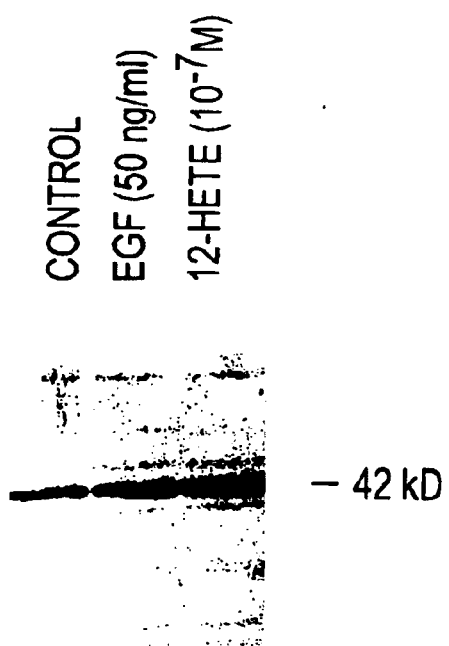
FIG. 9 is an immunoblot showing the effect of EGF and 12-HETE on VEGF expression in MCF-7 cells.
Figure 10:
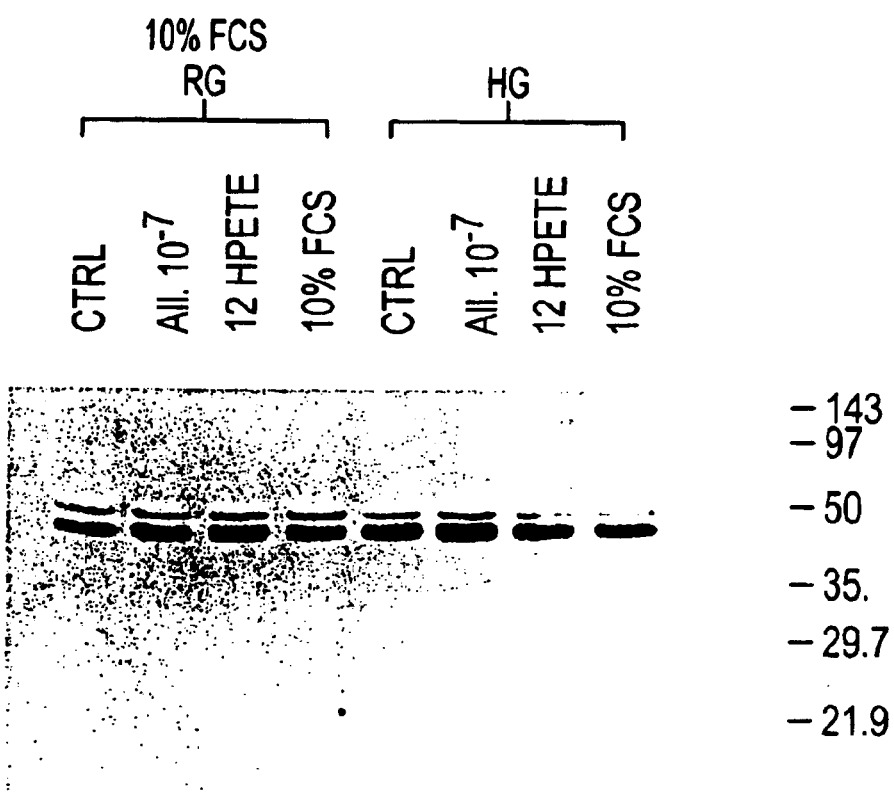
FIG. 10 is an immunoblot providing data on the effect of 12-HETE on VEGF expression in an immortalized human aortic smooth muscle cell line.

Description of FIGS. 8, 9 and 10

FIG. 8 illustrates the dose-dependent effect of platelet-derived growth factor (PDGF) on vascular endothelial growth factor (VEGF) protein (42 kD) expression in MCF-7 breast cancer cells. Nearly confluent MCF-7 cells were serum starved for 24 hours by placing in DME medium+ 0.4% FCS and 0.2% BSA. This medium was then freshly replaced and the cells incubated for another 24 hours with PDGF. At the end of the incubation, the cell monolayers were washed with ice-cold PBS, scraped into PBS and pelleted by centrifugation. The cell pellets were then lysed and equal amounts of protein (50 $\mu$g) subjected to electrophoresis and immunoblotting to detect VEGF using a specific antibody from Santa Cruz Biotechnology. Detection was by a chemiluminiscent technique. It is clearly seen that PDGF causes a dose-dependent increase in the expression of VEGF in the breast cancer cells.

FIG. 9 illustrates the effect of epidermal growth factor (EGF) and the 12-lipoxygenase product 12-HETE on VEGF protein expression in the MCF-7 breast cancer cell line MCF-7. MCF-7 cells were treated with EGF and 12-HETE for 24 hours and VEGF protein identified as described in the legend to FIG. 8. The figure shows that VEGF protein expression is not only induced by a breast cell mitogen such as EGF but also by the 12-LO product, 12-HETE. In fact, 12-HETE appears to be more potent than EGF in inducing VEGF indicating that 12-HETE has potent angiogenic properties.

FIG. 10 illustrates the effect of a 12-lipoxygenase product 12-HPETE on VEGF protein (42 kD) expression in an immortalized human aortic smooth muscle cell line (AIHSMC). The cells were serum starved for 24 hours and then placed in fresh medium along with 12-HPETE. Cells were incubated for five hours and VEGF protein was then identified in cell lysed as described in the legend to FIG. 8. Lane 3 shows that the 12-LO product, 12-HPETE causes an increase in the expression of the angiogenic agent, VEGF, in PVSMC when compared to the control in lane 1 as indicated in the figure.

FIGS. 8 and 9 report data in two human breast cancer cell lines MCF-7 and MDA MB that show that the 12-LO product 12-HETE at $10^{-7}$M and $10^{-6}$M increases VEGF protein expression. FIG. 10 shows that 12-HETE can increase VEGF protein in HVSMC.

In addition to the work reflected in FIGS. 8–10, it has now been discovered that AII, 12-HETE and hyperglycemia (HG) increase VEGF production in vascular smooth muscle cells (VSMC). Porcine and human VSMC were cultured for at least two passages under normal glucose (NG, 5.5 mM) or under HG conditions. VEGF protein expression was determined by Western blotting and VEGF mRNA by Northern blots. HG alone increased the level of VEGF mRNA (2.8-fold) and protein (3.2-fold). In addition, VEGF protein (45 K) and mRNA (3.7 Kb) expression were markedly increased by 4 hours of treatment with AII ($10^{-7}$M) in the cells cultured in HG (2.2- and 1.4-fold resp.). Furthermore, 12-HETE ($10^{-8}$M and $10^{-7}$M for 4 hours) increased the expression of both VEGF protein and mRNA in cells cultured under both NG as well as HG conditions. In addition, HG increased the secretion of VEGF into the medium as measured by a specific EIA (56.2±4 ng/ml NG vs 73±5 HG, p<0.02). AII and 12-HETE also increased VEGF secretion by 1.24 and 1.4-fold, respectively, as measured by EIA.

Consistent with this data, one aspect of this invention entails therapy to reduce breast and other cancer metastic potential as well as afflictions associated with diabetes (e.g., proliferative diabetic retinopathy and accelerated vascular disease) by reducing VEGF production, for example, through inhibition of the hi 12-LO pathway.

Role of the 12-LO Pathway in The Pathogenesis of Type I Diabetes

This aspect of this invention involves the role of 12-LO pathway activation in the pancreatic beta cell dysfunction or cytotoxicity in response to cytokines implicated in the pathogenesis of type I diabetes.

Description of FIGS. 11, 12 and 13

FIG. 11 illustrates the effects of 12-LO products on DNA synthesis in the insulin-producing rat beta cell line, RINm5F. DNA synthesis was studied using $^3$H-thymidine incorporation (luCi/ml) added for the last six hours (18–24 hours of experiment). The LO products were added to the cells in complete growth media for 24 hours. As demonstrated, 12-hydroxyeicosatetraenoic acid (12-HETE, $10^{-9}$M) and 12-hydroperoxyeicosatetraenoic acid (12-HPETE) reduced $^3$H-thymidine incorporation reflecting their effects to decrease DNA synthesis in this beta cell line.

FIG. 12 illustrates a western immunoblot of proteins isolated from the insulin producing rat beta cell line, RINm5F showing the effect of interleukin-1β on 12-LO protein expression. In these studies, 25 μg of protein was isolated from the cells grown for 16 hours in reduced serum-containing medium 0.4% alone or along with IL-1β (0.1 ng/ml). The results demonstrate a 2-fold increase in 12-LO protein expression after IL-1 treatment (lanes 2 and 4). Lane 7 shows the 12-LO standard showing the characteristic 72 kD 12-LO protein band using applicants peptide antibody which recognizes the rat, porcine and human forms of leukocyte-type 12-LO.

FIG. 13 illustrates the effects of IL-1β on 12-HETE production in rat islets.

Applicants have discovered that direct addition of the 12-LO products 12-S-HETE or 12-HPETE directly decreases cellular growth as reflected by decreased $^3$H thymidine incorporation or DNA synthesis in the rat pure beta cell line RIN-M5F. As shown in FIG. 11, concentrations of 12-LO products even as low as $10^{-9}$M decrease DNA synthesis. FIG. 12 demonstrates that human IL-1B at 0.2 ng increases leukocyte 12-LO protein expression approximately two fold in these RIN cells. FIG. 13 shows that IL-1B at 2.5 ng/ml markedly increases 12-LO activation in freshly isolated rat pancreatic islets as reflected by an increase in immunoreactive release of 12-S-HETE (92 pg/ml/40 islets basal to 250 pg/ml/40 islets.

Role of The 12-LO Pathway in The Development of Autoimmune Inflammatory and Atherosclerotic Disorders in Humans Increasing evidence suggests that cytokines such as $IL_1$, $IL_4$ and $IL_8$ play a role in the development of autoimmune, inflammatory and atherosclerotic disorders in humans.

Description of FIGS. 14–20

FIG. 14A illustrates the dose-dependent effect of the cytokine interleukin-1β on 12-LO mRNA expression in porcine aortic smooth muscle cells (PVSMC). Confluent PVSMC growth in normal glucose medium was serum depleted for 24 hours by placing in medium+0.2% BSA+ 0.4% FCS. This medium was then freshly replaced along with IL-1β and the cells incubated for a further 24 hours. At the end of the incubation, total RNA was extracted from the cells using RNA-STAT. This RNA was the subjected to reverse-transcriptase polymerase chain reaction (RT-PCR) to detect and quantitate leukocyte-type 12-LO mRNA (333 bp PCR product, upper panel) using our well established techniques. The expression of GAPDH mRNA 284 bp, lower panel) was used as an internal control for PCR and for quantitation. The figure clearly shows that IL-1β treatment leads to a dose-dependent increase in 12-LO mRNA expression (333 bp PCR product) while there is not much change in the internal control, GAPDH mRNA expression.

FIG. 14B illustrates the effect of the cytokine IL-4 on 12-LO mRNA expression in PVSMC. The ells were treated for 24 hours with IL-4 and 12-LO mRNA quantitated as described in the legend to FIG. 14A. It is clearly seen that IL-4 also increases 12-LO mRNA expression similar to IL-1β.

FIG. 14C illustrates the effect of the cytokine IL-8 on 12-LO mRNA expression in PVSMC. The cells were treated for 24 hours with IL-8 and 12-LO mRNA quantitated as described under legend 14A. The figure shows that IL-8 treatment of PVSMC leads to dose-dependent increase in 12-LO mRNA expression while there is no change in the internal control, GAPDH expression.

FIG. 15 illustrates the same RNA analyzed for the internal marker GAPDH.

FIG. 16 illustrates the effect of IL-4 on leukocyte-type 12-LO protein expression in PVSMC.

FIG. 17 illustrates the effect of IL-8 on leukocyte-type 12-LO protein expression in PVSMC.

FIG. 18 illustrates the effect of IL-4 on 12-LO activity in PSMC.

FIG. 19 illustrates the effect of IL-8 on 12-LO activity in PSMC.

FIG. 20 reflects the upregulation of hl 12-LO by IL-1, IL-4 and IL-8.

In addition to this work in islets, applicants have now demonstrated that $IL_1$, $IL_4$ and $IL_8$ can increase the mRNA expression of leucocyte type 12-LO in porcine and human aortic smooth muscle cells. Furthermore, applicants have evidence that 12-LO protein expression is similarly upregulated by these cytokines in porcine vascular smooth muscle. The cells were cultured in DME (normal glucose) and treated for 24 hours±cytokines in medium containing 0.2% BSA and 0.4% serum. Intracellular 12-LO enzyme activity was measured by HPLC, leukocyte-type 12-LO protein expression by immunoblotting and 12-LO mRNA by a specific reverse transcriptase polymerase chain reaction (RT-PCR). All three cytokines (2.5 ng/ml) caused a marked increase in 12-LO enzyme activity 51, 43 and 36% increase in 12-HETE HPLC peak for IL-1, -4 and -8 respectively). Further, all three cytokines (1–5 ng/ml) each led to a potent dose-dependent increase (2–5 fold) in 12-LO mRNA expression (340 bp PCR product). Treatment with these cytokines (0.5–5 ng/ml) also led to an increase (1.4–2.5-fold) in 12-LO protein expression 72 kD). In addition, all three cytokines (2.5 ng/ml) could induce a significant increase in PVSMC DNA synthesis (1.280.08, 1.67±0.11 and 1.3±0.07 fold increase in $^3$H thymidine incorporation with IL-1, -4, and -8 respectively, p<0.01).

Human vascular smooth muscle cells (HSMC) were also cultured in DME (normal glucose) and treated for 24 hours with $IL_1$, $IL_4$ and $IL_8$ in medium containing 0.2% BSA and 0.4% serum. Intracellular 12-LO enzyme activity in cell sonicates was measured by HPLC, leukocyte-type 12-LO protein expression by immunoblotting and 12-LO mRNA by a specific reverse transcriptase polymerase chain reaction (RT-PCR). Treatment of HSMC in low serum medium for 24 hours with IL-1, IL-4 or IL-8 (5 ng/ml) resulted in 7–10 fold increases in 12-LO mRNA expression relative to untreated cells. RNA from the same experiments was also analyzed for human 12-LO expression by a specific RT-PCR. No 15-LO mRNA was seen either in the basal or after cytokine addition.

These results suggest that these inflammatory cytokines have mitogenic effects in VSMC and that they are potent positive regulators of the 12-lipoxygenase pathway. Thus enhanced 12-LO activity and expression in response to these cytokines may be a key mechanism for cytokine-induced VSMC migration and proliferation observed in atherosclerosis. FIG. 14 shows the effects of $IL_1$, $IL_4$ and $IL_8$ on 12-LO mRNA expression in PVSMC cultured in normal (5.5 mM) and elevated (25 mM) glucoside. FIG. 15 represents the same RNA analyzed for the internal marker gene GAPDH showing all lanes have similar amounts of internal standard RNA. FIGS. 16 and 17 show increases in 12-LO protein expression in PVSMC by $IL_4$ and $IL_8$ respectively and FIGS. 18 and 19 reveal HPLC tracings showing selective increases in 12-LO protein activity in PSMC treated with $IL_4$ and $IL_8$ respectively. FIG. 20 shows evidence that $IL_1$, $IL_4$ and $IL_8$ can markedly upregulate leucocyte type 12-LO in human aortic SMC. In these same experiments, applicants were unable to demonstrate 15-LO expression in untreated or cytokine treated HSMC demonstrating the selective role of 12-LO as a potential mediator of cytokine action in vascular smooth muscle.

Role of 12-LO Pathway in The Pathogenesis of Type I and II Diabetes

Insulin dependent diabetes or type I diabetes is an autoimmune disease resulting in complete destruction of the insulin producing cells or beta cells in the pancreatic islet. Cytokines such as IL-1β are likely to be involved in this autoimmune process.

It has been discovered that IL-1β induces 12-LO protein and mRNA expression in RIN-M5F cells and 12-LO mRNA expression in rat islets. RIN-M5F cells treated for 16 hours with IL-1β (25, 50 and 100 ng/L) showed a dose dependent two-fold increase in expression of a porcine leukocyte form of 12-LO demonstrated by Western blots. A concomitant increase in 12-LO mRNA expression was seen at this time point using a highly sensitive competitive PCR assay. These transcriptional and translational events were paralleled by increased 12-LO pathway activity measured by radioimmunoassay for 12-HETE. Additionally, an inhibitor of inducible nitric oxide synthase (iNOS), N-monomethyl arginine (NMMA), was unable to prevent the IL-1β induced increase in 12-LO protein expression in RIN M5F cells, supporting the hypothesis that a pathway independent of inducible nitric oxide (NO) is present. Separate experiments using purified Sprague-Dawley rat islets also showed increased expression of 12-LO mRNA and enzyme activity.

In conclusion, 12-LO is a β-cell specific enzyme regulated at the transcriptional and translational level by cytokines like IL-1β.

Description of FIGS. 21–24

FIG. 21 reflects the increase in 12-LO mRNA expression in the pancreatic islets of increasingly diabetic rats.

FIG. 22 indicates that 12-LO mRNA expression in diabetic ZDF rat skeletal muscle is higher than from non-diabetic ZDF rats. The ZDF rat model has been proposed as an excellent animal model of spontaneous NIDDM (non-insulin dependent diabetes mellitus).

FIG. 23 presents data pertaining to rat-fibroblasts which overexpress the human insulin receptor.

FIG. 24 reflects a major change in the HETE/$PGI_2$ ratio in various diabetic groups.

NIDDM is a complex genetic disorder associated with a reduced ability of insulin to induce glucose transport in muscle ("insulin resistance") and a relative impairment of glucose-induced insulin secretion in pancreatic islets.

Consistent with another aspect of this invention, increased activity or expression of the 12-LO pathway is recognized as a common mediator of both of these abnormalities, such that blockade of the 12-LO pathway may prevent development of NIDDM.

The rationale for this statement includes:

1. Highly relevant data which evidences the presence of the leukocyte type 12-LO in pancreatic islets and skeletal muscle. The data in skeletal muscle is new and highly relevant. The available data in rat skeletal muscle and in human islet muscle RNA shows 12-LO expression using PCR analysis.

2. Evidence that 12-LO mRNA expression progressively increases in rat pancreatic islets from lean non-diabetic animals, to obese pre-diabetic and obese diabetic animals (see FIG. 21).

3. Data that 12-LO products added exogenously to rat pancreatic islets can reduce glucose-induced insulin secretion (45).

4. In vivo data (see Table 2) that urinary 12-HETE levels are much higher in male diabetic obese ZDF rats (a model of NIDDM) compared to lean ZDF non-diabetic rats. Interestingly, obese female ZDF rats which are phenotypically like pre-diabetic humans show intermediate levels of 12-HETE in urine.

TABLE 2

Urinary 12-HETE in ZDF Rats

|   |   | pg/total urine vol. |
|---|---|---|
| Diabetic Male | Obese Ctrl | 2022 ± 372 |
| Non-diabetic | Female Obese Ctrl | 1007 |
|  | Female Obese Mg2+ | 86 |
| Non-diabetic | Lean Male | — |
|  | Lean Female | — |

5. Data which indicates that 12-LO mRNA expression in diabetic ZDF rat skeletal muscle is much higher than levels in skeletal muscle from non-diabetic ZDF rats (lane 11 vs lane 21 in FIG. 22). Interestingly, 12-LO mRNA levels in skeletal muscle are also higher in obese female ZDF rats that are prone to get diabetes. In this figure, the 312 bp band is the 12-LO band while the 281 bp band is the 12-LO competitor. This data represents true competitive PCR analysis of 12-LO mRNA. Applicants also have data in the ZDF heart that suggests that 12-LO expression is also higher in diabetic cardiac tissue.

In addition to this work, 12-LO RNA and protein expression in two NIDDM models, ZDF (Zucker diabetic fatty) rats and GK (Goto Kyoto) rats have been evaluated. A specific quantitative polymerase chain reaction (PCR) assay was used to measure 12-LO mRNA expression and Western blotting using an anti 12-LO peptide antibody was used to evaluate 12-LO protein expression. The GK rat model of NIDDM demonstrated an increased blood glucose concentration compared to age-marched Wistar controls (8.7±0.7 vs 4.8±0.2 mM, p<0.01). However, plasma insulin and body weight were similar between the GK and Wistar rats. 12-LO mRNA expression was 4-fold greater in heart from GK rats compared to Wistar (0.48±0.1×$10^5$ molecules per μg RNA in Wistar vs 1.9±0.4×$10^5$ in GK p<0.02). 12-LO mRNA expression in soleus muscle was over 5-fold greater in GK vs Wistar rats (0.6±0.1 Wistar vs 3.1±0.76 GK). The ZDF obese rats demonstrated an increase in blood glucose concentration and weight compared to the ZDF lean controls (558±75 vs 170±5 mg/dl and 390±7 vs 343±7 gram respectively). 12-LO mRNA was analyzed in the heart, red and white quadriceps muscle in the diabetic and lean ZDF rats. 12-LO mRNA expression was increased by 4–7 fold in the diabetic obese ZDF rats compared to the lean ZDF controls. 12-LO protein expression was similarly increased in heart tissue (5-fold) in the diabetic ZDF vs the lean ZDF controls. These data reflect that muscle 12-LO expression is markedly increased in both lean and obese rat models of NIDDM.

6. Data which indicates that 12-HETE levels in $L_6$ muscle cells are increased in the presence of glucose. $L_6$ muscle cells are skeletal muscle cells from rats which have been used to investigate the mechanisms of insulin action. When $L_6$ muscle cells are incubated in xylose (5.5, mM), they are much more responsive to insulin when compared to cells in regular glucose (5.5 mM) or high glucose (25 mM). Table 3 below demonstrates higher levels of 12-HETE release in the media (pg/ml) or in the cells (pg/total cells) in regular glucose (Rg) or high glucose (HG) conditions. Thus, elevated 12-Lipoxygenase products, such as 12-HETE, appear to play an important role in reduced insulin metabolic actions caused by high glucose.

TABLE 3

Effect of Glucose on 12-HETE in $L_6$ Muscle Cells

| Cells | Condition | | |
|---|---|---|---|
| $L_6$ | Xylose | Rg | Hg |
| pg/ml (n = 2) | 53.2 | 101.8 | 110.3 |
| pg/total cells (n = 2) | 398 | 472 | 620 |

7. Baicalein, a selective 12-LO inhibitor, can prevent glucose-induced insulin resistance. To perform these studies, applicants cultured rat-1-fibroblasts that have been engineered to contain the human insulin receptor for ten days in high glucose (25 mM). For the last 24 hours, the cells were cultured with $10^{-6}$M baicalein. The marked bands represent the phosphorylated beta sub-unit of the human insulin receptor (FIG. 23). As the band becomes lighter, it represents reduced insulin action. Lane 1 represents the insulin receptor phosphorylation in normal glucose (5.5 mM) vs the reduced insulin action in lane 5 (25 mM glucose). Lane 6 represents the insulin receptor phosphorylation in 25 mM glucose when 12-LO pathway was blocked with baicalein showing restoration of insulin receptor phosphorylation.

In addition to this work, applicants have discovered that 12-HETE directly inhibits insulin-induced receptor phosphorylation. As shown in FIG. 27, a clear increase in phosphorylation of the 97 kD beta subunit of the insulin receptor occurs when insulin is present. This is demonstrated by a darker band at 97 kD in lane 4 (insulin-treated) vs Lane 1 (control, non-insulin-treated). 12-HETE ($10^{-7}$M concentration) did not directly alter basal insulin receptor phosphorylation (lane 2). In contrast, 12-HETE markedly reduced insulin-induced receptor phosphorylation of the beta subunit of the human insulin receptor. This is demonstrated by a reduced band intensity in lane 5 (12-HETE $10^{-7}$M) vs. Lane 4 (no 12-HETE addition).

Since insulin receptor phosphorylation is one of the early important steps in insulin action, these results suggest that products of the 12-LO pathway can lead to reduced insulin action. This data suggests that increased expression or activity of the 12-LO pathway appears to play a key role in the insulin resistance in non-insulin dependent forms of diabetes.

8. Data which indicates that glucosamine, a proposed major mediator of glucose toxicity in terms of reduced insulin action and vascular disease, increases 12-LO product formation in smooth muscle cells. The role of glucosamine in leading to insulin resistance has recently been demonstrated in intact animals (Baron et al., *J. Clin. Invest.*, 96:2792–2801 (1995)) and in insulin responsive tissues in vitro (e.g., muscle—Robinson et al., *Diabetes*, 42:1333–46 (1993); and fat—Marshall et al., *J. Biol. Chem.*, 266:4706–4712 (1991). Furthermore, glucosamine is thought to be a major mediator of glucose-induced vascular disease (Daniels et al., *Mol. Endocrinol.*, 7:1041–1048 (1993)). While not wishing to be bound by a particular theory, it is believed that glucosamine impairs insulin-induced glucose uptake by blocking the normal action of Glut 4, the major glucose transporter linked to insulin ability to transport glucose.

Porcine vascular smooth muscles cells (PVSMC) were cultured in the presence of glucosamine (7.5 mM) for 24 hours. New media was then added with glucosamine (7.5 mM) for 25 minutes. The cells and media above the cells were collected and 12-HETE was measured using RIA. A very large increase in 12-HETE release into the media in cells cultured in glucosamine compared to those in normal glucose (6.48±1.2 pg/ml 12-HETE release in normal glucose vs. 20.6±3.6 pg/ml released in glucosamine n=4) was observed. Furthermore, cell associated 12-HETE was higher in glucosamine treated cells (735.9±67 pg/cell incubate normal glucose vs. 1225±112 pg in glucosamine). These data suggest that 12-LO products such as 12-HETE may be important factors leading to insulin resistance.

9. Data which indicates that high fat feeding simultaneously leads to impaired insulin action and induction of 12-LO protein expression in muscle. The mouse model used was a transgenic mouse over expressing the Glut 4 transporter (Pfizer Pharmaceuticals). As can be seen in FIG. 28, high fat feeding clearly led to impaired glucose tolerance, which is a clear indication that the animals were insulin resistant. FIG. 28a shows a higher glucose level at every point on the oral glucose test curve in the fat fed mice than in the control. The bar graph of FIG. 28b demonstrates a significantly greater area under the glucose tolerance curve in the high fat fed group than in the control.

In four of the animals on the high fat diet, 12-LO protein expression in cardiac muscle was evaluated and compared to the levels in animals on the control diet. 12-LO protein expression was measured using 12-LO peptide antibody and Western blotting. The summary of the data is shown in Table 4 below. The striking results show much higher levels of 12-LO protein (using densitometric analysis of blots) in animals on the high fat diet. These in vivo results suggest that increased 12-LO expression or activity plays a key role in leading to insulin resistance.

TABLE 4

Densitometry Result Comparisons of
12-LO Protein Expression in Heart Muscle Western Blot
Mann-Whitney Test Mann-Whitney U-statistic = 0.000
U' = 16.000
Sum of ranks in Control Male = 10.000
Sum of ranks in Fat Male = 26.000
The two-tailed P value is 0.0286, considered significant.

|  | Control Diet | High Fat Fed Diet |
|---|---|---|
| Parameter: | Control Male | Fat Male |
| Mean: | 2.925 | 12.897 |
| # of points: | 4 | 4 |
| Std deviation: | 1.041 | 14.636 |
| Std error: | 0.5203 | 7.318 |
| Minimum: | 1.890 | 5.390 |
| Maximum: | 4.370 | 34.850 |
| Median: | 2.720 | 5.675 |
| Lower 95% CI: | 1.269 | −10.388 |
| Upper 95% CI: | 4.581 | 36.183 |

10. Data which indicates that high magnesium (Mg) feeding markedly reduces 12-LO gene expression and 12-HETE levels. Mg deficiency has been associated with experimental and human insulin resistance. Moreover, increased dietary Mg has been associated with reduced development of diabetes in ZDF rats as well as in humans, and Mg supplementation can improve insulin response and actions in humans with NIDDM.

It has now been discovered that high Mg feeding markedly reduces 12-LO gene expression and 12-HETE levels. High Mg diets (Purina 5008 diet containing 1% Mg) were fed to one group of ZDF obese (diabetic fatty) male rats while control diets (Purina 5008 plus 0.2% Mg) were fed to another group. As can be seen in Table 5, the high Mg feeding group possessed significantly lower urinary 12-HETE concentrations as measured by RIA (methods described in J. Clin. Endocrin. Metab., 67:584–591 (1988) and J. Clin. Invest., 80:1763–1769 (1987)) than the control group. High Mg feeding also reduced 12-LO mRNA expression in muscle from diabetic ZDF rats.

TABLE 5

Urinary 12-HETE Excretion
Rate in ZDF Rat Models

| ZDF PAT | 12-HETE (pg/mm) |
|---|---|
| ZDF lean (n = 4) | $^a$0.4 ± 0.07 |
| ZDF obese (n = 6) | 6.12 ± 1.2 |
| ZDF obese (n = 6) with h.Mg diet | $^b$3.72 ± 0.5 |

Values are mean ± SE.
n is the number of rats.
Values in ZDF lean group and ZDF obese with high magnesium diet group are different from ZDF obese group at
$^a p < 0.001$ and
$^b p < 0.05$ respectively.

11. Human data shows increased urinary levels of 12-HETE in people with NIDDM. Levels of 12-HETE are particularly high in diabetics showing evidence of proteinuria. These results suggest that 12-LO activation may be involved in renal disease in diabetes.

Vascular tissue from diabetic animals and man metabolize arachidonic acid differently from normals. $PGI_2$ is a vasodilator, antithrombolic, and renin secretagogue while 12-hydroxyeicosatetraenoic acid (12-HETE) is proinflammatory and inhibits cyclooxygenase (CO). Applicants earlier reported a prostacyclin ($PGI_2$) deficiency in diabetics with hyporeinemic hypoaldosteronism (HH) (46). Applicants explored the production of the CO product, $PGI_2$ and the lipoxygenase (LO) product, 12-HETE in NIDDM patients with normal renal function (NR), those with microalbuminuria (MiA0, macroabluminuria (MaA) and HH patients. $PGI_2$ (6 keto $PGF^1$) and 12-HETE were measured in urine by HPLC followed by RIA using published methods. Results are:

|  | $PGI_2$ (ng/gm Creat) | 12-HETE (ng/gm Creat) | Ratio |
|---|---|---|---|
| Controls (N = 17) | 64 ± 16 | 43 ± 9 | 0.7 ± 0.3 |
| Diabetics (NR) (N = 8) | 64 ± 9 | 122 ± 34* | 2.0 ± 0.5 |
| Diabetics (MiA) (N = 14) | 75 ± 10 | 226 ± 60* | 3.8 ± 1.3 |
| Diabetics (MaA (N = 9) | 48 ± 7** | 352 ± 152* | 8.1 ± 5.4 |
| Diabetics (HH) (N = 5) | 39 ± 5 | 240 ± 35*† | 6.8 ± 2.4 |

†From previously stored samples
*p < 0.01 vs controls
**p < 0.05 vs diabetics

This data suggests that (1) an increase in the 12-LO product 12-HETE is observed in all NIDDM which progresses with renal disease; (2) diabetic renal disease with albuminuria is associated with suppression of $PGI_2$ production; and (3) HH is a disorder of $PGI_2$ suppression and 12-HETE excess.

Applicants further study has measured urinary (renal vascular) production of both $PGI_2$ and 12-HETE in patients with varying degrees of diabetic renal involvement.

In the group of NIDDM patients with normal renal function based on creatinine clearance and urinary albumin measurements, $PGI_2$ excretion was not different from normal controls. The group with microalbuminuria were divided into those with hypertension and normotensive. However, no difference in $PGI_2$ excretion was noted. Nevertheless the microalbuminuria group had significantly lower $PGI_2$ excretion rates. The patients with macroalbuminuria and reduced creatinine clearance similarly had reduced $PGI_2$ excretion. $PGI_2$ excretion rates were reduced in the macroabluminuria and HH group.

12-HETE values were markedly increased in NIDDM patients with or without microalbuminuria compared with normal controls. 12-HETE excretion values were also significantly increased in the macroabluminuria group as well as in the HH group.

Low dose calcium infusions have been previously shown to increase $PGI_2$, probably via activation of tissue phospholipases. When a three hour infusion of calcium gluconate was administered to normal subjects, there was a highly significant increase in both $PGI_2$ and 12-HETE. However, when administered to NIDDM patients with microalbuminuria, there was no increase in $PGI_2$ but a further stimulation of the already increased 12-HETE values. This supports the concept that a defect in prostacyclin formation exists in NIDDM.

12-HETE/$PGI_2$ ratios were calculated as an additional approach to define whether in NIDDM there is an alteration in the LO/CO pathways. As shown in FIG. 24, there is a major change in the HETE/$PGI_2$ ratio in all diabetic groups. The mean value is significantly increased in NIDDM patients with normal renal function and is further altered in patients with macroalbuminuria and HH patients. However, these differences were not significantly different between the NIDDM groups due to the variability within each group.

Applicants data appears to exclude renal function per se, GFR or hypertension as a cause of the deranged eicosanoid excretion values. While the origin of $PGI_2$ and 12-HETE in urine has not been fully settled, studies using extrarenal CO inhibitors and lack of excretion of tracer $PGI_2$ and 12/15-HETE following systemic injection, suggests that the kidney is the major source of these compounds in urine (47–49). HETEs can be generated in vascular tissue as well as from inflammatory cells. (50–51). However, there is no evidence for macrophage/leukocytes infiltration into the kidney in NIDDM with only incipient glomerular and vascular disease.

In agreement with in vitro and animal model studies cited earlier, applicants results suggest that early in diabetes mellitus, there is fixed prostacyclin production which falls to lower values with diabetic renal vascular/glomerular disease. This occurs in a state where the LO product 12-HETE is increased early in diabetes mellitus prior to development of microalbuminuria. These observations could be of considerable importance in the etiology of diabetic vascular disease since the HETEs are mitogenic proinflammatory, vasoconstrictive, and stimulate angiogenesis (52–53). With respect to the HH syndrome, applicants new data suggests that increased HETE production may be an early abnormality in suppressing $PGI_2$ formation and renin biosynthesis and secretion. The etiologic event in diabetes explaining vascular disease is not known. However, recent studies suggest that hyperglycemia per se has a number of metabolic consequences including enhanced eicosanoid generation via protein kinase C and activation of calcium dependent phospholipases, major mediators of AA release (54).

In summary, whether cause or effect, very early involvement of the kidney in diabetes is associated with fixed or suppressed production of prostacyclin, with increase in the vasculotoxic lipoxygenase product 12-HETE. This conclusion is now suggested by both in vitro studies and in vivo studies in man. This suggests pharmacologic intervention early in the diabetic state to block this derangement.

Role of 12-Lipoxygenase Products in Glucose-Induced Monocyte Binding to Human Aortic Endothelial Cells The rate of atherosclerosis is accelerated in humans with diabetes mellitus (DM). Applicants recently published evidence that high glucose (HG) exposure of human aortic endothelial cells (HAEC) selectively increases monocyte (MO) but not neutrophil binding (56). HG exposure to EC can increase arachidonic acid (AA) release and lipoxygenase (LO) production formation. In the current study, applicants evaluated the role of 12- and 15-LO products in MO binding to HAEC. Culture of HAEC in HG (25 mM) for two passages increased MO binding compared to cells maintained in 5.5 mM glucose (239±30 cells/field HG vs 111±7, $p<0.01$). Phenidone ($10^{-6}$M), an inhibitor of the 12-LO pathway (50 percent inhibition of HG-induced binding, $p<0.05$). HG culture of HAEC significantly increased both 12- and 15-hydroxyeicosatrienoic acids (HETEs) using applicants HPLC and RIA methods. 12(S)-HETE added to HAEC cultured in 5.5 mM glucose increased MO binding (66±6 cells/field control vs 114±4 12-HETE $10^{-10}$M, $p<0.01$). Another novel 12-LO product 12(R)-Hydroxyeicosatrienoic acid was even more potent showing effects on MO binding at $10^{-11}$ and $10^{-12}$M. In contrast, 15(S)-HETE added at concentrations ranging from $10^{-6}$ to $10^{-12}$M did not stimulate MO binding to HAEC. In summary, (1) elevated glucose increases MO binding to HAEC and this effect can be reduced by blockade of the LO pathway; (2) 12 but not 15-LO products, can increase MO binding. Since a leucocyte type 12-LO is expressed in HAEC, these results support the role of 12-LO activation in glucose-induced MO binding to human endothelium.

Applicants have also demonstrated that high fat "cafeteria" diets increase leukocyte 12-LO in rat hearts and that diabetic (GK) rats have a higher 12-LO in heart compared to normal (Wistar) animals (see FIGS. 25 and 26).

Diagnostic Assays

Application PCT/US94/00089 reports that antibodies would circulate in patients at risk for developing disease states for which hl 12-LO or its pathway products such as HETE or 12-HPETE are the etiological agent. Accordingly, another aspect of this invention includes assays, e.g., of the ELISA type in which hl 12-LO protein, or a related material such as HETE is utilized as an immunogen. Such tests are useful to diagnose any of the disease states mediated by the activation or expression of hl 12-LO.

Bibliography

1. Geisterfer, A. A., et al., *Circ. Res.* (1988) 62:749–756.
2. Izumi, T., et al., *Proc. Natl. Acad. Sci. USA* (1990) 87:7477–7481.
3. Gu, J., et al., *Endocrinology* (1994) 143:70–77.
4. Samuelsson, B., *Science* (1987) 237:1171–1176.
5. Sparrow, C. P., et al., *J. Lipid Res.* (1988) 29:745–753.
6. Steinberg, D., *New Eng. J. Med.* (1989) 320:915–924.
7. Berk, B. C., *Hypertension* (1989) 13:305–314.
8. Schwartz, S. M., *Physiol. Rev.* (1990) 70:1177–1209.

9. Nakao, J., et al., *Atherosclerosis* (1982) 44:339–342.
10. Natarajan, R., et al., *J. Clin. Endocrinol. Metab.* (1988) 67:584–591.
11. Nadler, J. L., et al., *J. Clin. Invest.* (1987) 80:1763–1769.
12. Natarajan, R., et al., *Endocrinology* (1992) 131:1174–1180.
13. Funk, c. D., et al., *Proc. Natl. Acad. Sci. USA* (1990) 87:5638–5642.
14. Yoshimoto, T., et al., *Proc. Natl. Acad. Sci. USA* (1990) 87:2142–2146.
15. DeMarzo, N., et al., *Am. J. Physiol.* (1992) 262:L198–L207.
16. Rapoport, S. M., et al., *Eur. J. Biochem.* (1979) 96:545–561.
17. Sigal, E., et al., *J. Biol. Chem.* (1988) 263:5328–5332.
18. Nadel, J. A., et al., *J. Clin. Invest.* (1991) 87:1139–1145.
19. Pitas, R. E., *Arteriosclerosis* (1981) 1:177–185.
20. Gown, A. M., et al., *Am. J. Pathol.* (1986) 125:191–207.
21. Fogelman, A. M., et al., *J. Lipid Res.* (1988) 29:1243–1247.
22. Sigal, E., et al., *Biochem. Biophys. Res. Commun.* (1988) 157:457–464.
23. Tso, J. Y., et al., *Nucleic Acids Res.* (1985) 13:2485–2502.
24. Laemmli, N. K., *Nature*, (1970) 227:680–685.
25. Towbin, H., et al., *Proc. Natl. Acad. Sci. USA* (1979) 76:4350–4354.
26. Esteban, J. M., et al., *Modern Pathology* (1990) 3:192–197.
27. Lopez, S., et al., *Biochem. Biophys. Acta* (1993) 1170:17–24.
28. Conrad, D. J., et al., *Proc. Natl. Acad. Sci. USA* (1992) 89:217–221.
29. Stern, N., et al., *Am. J. Physiol.* (1989) 257:H434–H443.
30. Funk, C. D., et al., *J. Biol. Chem.* (1985) 260:7481–7488.
31. Natarajan, R., et al., *Biochem. Biophys. Res. Commun.* (1992) 187:552–560.
32. Kato, H., et al., *J. Hypertens.* (1001) 9:17–22.
33. Daemaen, M J A P, et al., *Circ. Res.* (1991) 68:450–456.
34. Osterrieder, et al., *Hypertension* (1991) 18 (Supp. II):II-60–II-64.
35. Natarajan, R., et al., *Hypertension* (1994) 23 (Supp. I):I142–I147.
36. Haliday, E. M., *Embo. J.* (1991) 10:109–115.
37. Yu, C. L., *Mol. Cell Biol.* (1990) 10:6683–6689.
38. Rao, G. N., et al., *Oncogene* (1993) 8:2759–2764.
39. Ylä-Herttuala, S., et al., *Proc. Natl. Acad. Sci. USA* (1990) 87:6959–6963.
40. Ylä-Herttuala, S., et al., *J. Clin. Invest.* (1991) 87:1146–1152.
41. Parthasarathy, S., *J. Clin. Invest.* (1992) 89:1618–1621.
42. Mathur, S., et al., *Biochim. Biophys. Acta* (1985) 837:13–19.
43. Reinard, O., et al., *Biochem. Biophys. Res. Comm.* (1989) 161:883–891.
44. Hajjar, D., et al., *J. Biol. Chem.* (1987) 262:6976–6981.
45. Nathan, M., Pek, B. Lipoxygenase-generated icosanoids inhibit glucose-induced insulin release from rat islets. Prost leukotrienes and essential fatty acids. (1990) 40:21–25.
46. *New Eng. J. Med.*, (1986) 314:1015.
47. Fitzgerald, G., et al., *Circ. Res.* (1983) 67:1174–7.
48. Ciabattoni, G., et al., *N. Eng. J. Med.* (1984) 310:279–83.
49. Clouet, P., et al., *Prostaglandin* (1991) 42:39–45.
50. Greenwald, J. E., et al., *Nature* (1979) 281:588–89.
51. Larrue, J., et al., *Biochem. Biophys. Res. Commun.* (1983) 112:242–49.
52. Setty, B., et al., *J. Biol. Chem. JBC* (1987) 262:17613–22.
53. Yoshimoto, T., *Proc. Natl. Acad. Sci. USA* (1990) 87:2142–46.
54. DeRubertis, F., *Diabetes* (1994) 43:1–8.
55. Alanko, J., et al., *Biochem. Pharm.* (1994) 10:1979).
56. *Diabetes* 43:1103–1107 (1994).

What is claimed is:

1. A method for diagnosing a disease state in a patient in which 12-lipoxygenase, distinct from that found in human platelets and distinct from human 15-lipoxygenase, is an etiological agent, which comprises:
   (i) obtaining a physiological specimen from said patient; and
   (ii) determining whether said 12-lipoxygenase is present in said specimen at an elevated level;
wherein the presence of said 12-lipoxygenase at an elevated level indicates said disease state.

2. The method of claim 1 in which said disease state is selected from the group consisting of an inflammatory condition, an autoimmune condition, atherosclerosis, cancer growth, cancer metastasis, dysfunctional secretion of insulin in non-insulin dependent diabetics, glucose-induced oxidative stress and the development of end-organ dysfunction or damage.

3. The method of claim 2, wherein said disease state is atherosclerotic vascular disease, human breast cancer, or Type II diabetes.

4. The method of claim 1 wherein said physiological specimen is selected from the group consisting of vascular smooth muscle cells, adrenal cells, aortic endothelial cells, arterial endothelial cells, monocytes, pancreas tissue, breast tissue, renal tissue, or a tumor.

5. A method of diagnosing a disease state in a patient in which 12-HETE or 12-lipoxygenase is an etiological agent, which comprises:
   (i) obtaining a physiological specimen from said patient; and
   (ii) determining whether said etiological agent is present in said specimen at an elevated level;
wherein said 12-lipoxygenase is distinct from that found in human platelets and distinct form human 15-lipoxygenase, wherein the presence of said etiological agent at an elevated level indicates said disease state and wherein the disease state is selected from the group consisting of atherosclerosis, cancer growth and cancer metastasis.

6. The method of claim 5, wherein said disease state is selected from the group consisting of atherosclerotic vascular disease and human breast cancer.

7. The method of claim 5, wherein said physiological specimen is selected from the group consisting of vascular smooth muscle cells, adrenal cells, aortic endothelial cells, arterial endothelial cells, monocytes, breast tissue, renal tissue and a tumor.

* * * * *

SEQUENCE LISTING

<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: 5' Primer for
      human 15-LO

<400> SEQUENCE: 1
aactcaaggt ggaactaccg gag                                           23

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: 3' Primer for
      human 15-LO
<221> NAME/KEY: variation
<222> LOCATION: (8)
<223> OTHER INFORMATION: n = inosine

```
<400> SEQUENCE: 2
atatagtntg gccccagcca tattc                                              25

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Probe for
      human 15-LO

<400> SEQUENCE: 3
aggctcagga cgccgttgcc                                                    20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: 5'Primer for
      porcine leukocyte 12-LO

<400> SEQUENCE: 4
ttcagtgtag acgtgtcgga g                                                  21

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: 3' Primer for
      porcine leukocyte 12-LO

<400> SEQUENCE: 5
atgtatgccg gtgctggcta tattt                                              25

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Probe for
      porcine leukocyte 12-LO

<400> SEQUENCE: 6
tcaggatgcg gtcgccctcc ac                                                 22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: 5' Primer for
      human GAPDH

<400> SEQUENCE: 7
cccatcacca tcttccagga g                                                  21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: 3' Primer for
      human GADPH
```

-continued

```
<400> SEQUENCE: 8
gttctcatgg atgaccttgg c                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Probe for
      human GADPH

<400> SEQUENCE: 9
ctaagcagtt ggtggtgcag g                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: 5' Primer for
      human platelet 12-LO

<400> SEQUENCE: 10
gatgatctac ctccaaatat g                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: 3' Primer for
      human platelet 12-LO

<400> SEQUENCE: 11
ctggccccag aagatctgat c                                              21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Probe for
      human platelet 12-LO

<400> SEQUENCE: 12
gtttgagggc catctccaga gc                                             22
```